US012672893B2

(12) United States Patent
Sun et al.

(10) Patent No.: US 12,672,893 B2
(45) Date of Patent: Jul. 7, 2026

(54) TISSUE CUTTER AND MINIMALLY INVASIVE INTERVENTIONAL SURGICAL INSTRUMENT

(71) Applicant: JEDICARE MEDICAL CO., LTD., Shanghai (CN)

(72) Inventors: Fei Sun, Shanghai (CN); Shi Xin Liu, Shanghai (CN); Ri Yue Huang, Shanghai (CN)

(73) Assignee: JEDICARE MEDICAL CO., LTD., Shanghai (CN)

( * ) Notice: Subject to any disclaimer, the term of this patent is extended or adjusted under 35 U.S.C. 154(b) by 683 days.

(21) Appl. No.: 18/002,130

(22) PCT Filed: Jun. 7, 2021

(86) PCT No.: PCT/CN2021/098558
§ 371 (c)(1),
(2) Date: Dec. 16, 2022

(87) PCT Pub. No.: WO2021/254189
PCT Pub. Date: Dec. 23, 2021

(65) Prior Publication Data
US 2023/0338053 A1    Oct. 26, 2023

(30) Foreign Application Priority Data
Jun. 18, 2020    (CN) .......................... 202010559520.1

(51) Int. Cl.
*A61B 17/3205* (2006.01)
*A61B 17/00* (2006.01)
*A61B 17/34* (2006.01)

(52) U.S. Cl.
CPC .. *A61B 17/32056* (2013.01); *A61B 17/00234* (2013.01); *A61B 17/34* (2013.01)

(58) Field of Classification Search
CPC .......... A61B 17/3205; A61B 17/32056; A61B 17/221; A61B 17/12172; A61B 17/12109;
(Continued)

(56) References Cited

U.S. PATENT DOCUMENTS 5,201,740 A * 4/1993 Nakao .............. A61B 17/32056
606/45
5,279,548 A 1/1994 Essig et al.
(Continued)

FOREIGN PATENT DOCUMENTS

CN    102973332 A    3/2013
CN    107899124 A    4/2018
(Continued)

OTHER PUBLICATIONS

International Search Report and Written Opinion of the International Searching Authority in corresponding International Application No. PCT/CN2021/098558 mailed Aug. 30, 2021 (10 pages).
(Continued)

*Primary Examiner* — Katherine H Schwiker
(74) *Attorney, Agent, or Firm* — Jeffri A. Kaminski; Venable LLP

(57) ABSTRACT

A tissue cutter includes a tissue cutting stent and a first reefing thread. The tissue cutting stent is expandable in a radial direction. The expanded tissue cutting stent is loudspeaker-shaped gradually opening from a proximal end to a distal end, and a loudspeaker-shaped accommodating space is formed inside the expanded tissue cutting stent. The tissue cutting stent is provided with a plurality of first threading holes at the distal end, and the plurality of first threading holes is arranged along a circumferential direction of the tissue cutting stent. The first reefing thread passes through the plurality of first threading holes. The first reefing thread has opposite first and second ends. The first end is secured
(Continued)

to a starting threading hole in the plurality of first threading holes.

29 Claims, 15 Drawing Sheets

(58) Field of Classification Search
CPC .... A61B 17/320758; A61B 17/320725; A61B 17/320783; A61B 17/320791; A61B 2017/2215; A61B 2017/2217; A61B 2017/22001; A61B 2017/22035; A61B 2017/320044; A61B 2017/320064; A61B 2017/320733; A61B 18/1487; A61B 2018/00267; A61B 2018/00601; A61B 2018/1407; A61F 2/013
See application file for complete search history.

(56) References Cited

U.S. PATENT DOCUMENTS

| | | | |
|---|---|---|---|
| 6,506,166 B1 | 1/2003 | Hendler et al. | |
| 6,748,953 B2 | 6/2004 | Sherry et al. | |
| 2004/0059372 A1* | 3/2004 | Tsugita | A61F 2/013 |
| | | | 606/108 |
| 2004/0158261 A1 | 8/2004 | Vu | |
| 2006/0195118 A1* | 8/2006 | Richardson | A61B 17/221 |
| | | | 606/113 |
| 2008/0103508 A1 | 5/2008 | Karakurum | |
| 2011/0319917 A1* | 12/2011 | Ferrera | A61B 17/320725 |
| | | | 606/159 |
| 2013/0345739 A1* | 12/2013 | Brady | A61B 17/320725 |
| | | | 606/200 |
| 2019/0000492 A1* | 1/2019 | Casey | A61B 17/22031 |

FOREIGN PATENT DOCUMENTS

| | | |
|---|---|---|
| CN | 108784896 A | 11/2018 |
| CN | 109310452 A | 2/2019 |
| CN | 109498147 A | 3/2019 |
| CN | 110494183 A | 11/2019 |
| CN | 111166463 A | 5/2020 |
| WO | 2019064306 A1 | 4/2019 |
| WO | 2019085841 A1 | 5/2019 |

OTHER PUBLICATIONS

Chinese Second Office Action in corresponding Chinese Application No. 202010559520.1 dated Jul. 31, 2023 (21 pages).
Chinese Decision on Rejection in corresponding Chinese Application No. 202010559520.1 dated Dec. 19, 2023 (17 pages).
Chinese Office Action in corresponding Chinese Application No. 202010559520.1 dated May 5, 2023 (25 pages).

* cited by examiner a proximal end a distal end

1"

a proximal end

20"

30"

a distal end

1

TISSUE CUTTER AND MINIMALLY INVASIVE INTERVENTIONAL SURGICAL INSTRUMENT

CROSS-REFERENCE TO RELATED APPLICATIONS

This application is a U.S. National Stage application of PCT/CN2021/098558, filed Jun. 7, 2021 and published on Dec. 23, 2021, as WO 2021/254189, which claims the benefit of Chinese Patent Application No. 202010559520.1 filed Jun. 18, 2020, all of which are hereby incorporated by reference in their entireties.

TECHNICAL FIELD

The present invention relates to the field of medical instrument, specifically, to a tissue cutter and a minimally invasive interventional surgical instrument.

BACKGROUND

With the rapid spread and cost reduction of imaging devices (such as CT/MRI (magnetic resonance imaging)), early tumors can be detected when patients are asymptomatic with the help of imaging devices, which provides the possibility for early diagnosis, early treatment and reduction of mortality rate of patients with tumors. For many early tumors found in solid organs, such as lung cancer, liver cancer, breast cancer, prostate cancer and so on, the corresponding radical treatment technique is mainly surgical resection.

Surgical resection apparatus used today mainly includes minimally invasive surgical instruments such as thoracoscopes or laparoscopes, but even these minimally invasive surgical instruments still create a larger incision on the body surface and on the target tissues and organs of human. Taking a single-port thoracoscopy as an example, an incision of at least 3 cm on the body surface is required to complete a surgery. The reason is that the thoracoscopy requires multiple instruments (various forceps, scissors, hooks, and anastomoses) to insert into the body through the incision and operate simultaneously in order to resect and remove early tumors.

Since a larger incision is to be created, general anesthesia for patients is required, and the instruments needed and resection maneuvers conducted during the surgical procedure are complicated. All of these result in the inability to use imaging devices and mere reliance on human eyes during the surgical procedure. However, human eyes cannot accurately identify the exact locations of the lesions within tissues and organs, so that an extensive resection is often required during the surgical procedure to ensure resection of the target lesions. Generally, only linear cutting can support such an extensive resection, which may cause resection of a larger number of normal tissues and organs during the surgical procedure.

The larger the surgical incision is, the slower the patients' recovery will be. The more the normal tissues and organs are resected, the greater the impact on the patients' long-term postoperative health will be. To improve the life quality of patients, it is necessary to provide a minimally invasive treatment with less traumas.

SUMMARY

In order to solve the problems at least partially in prior arts, according to an aspect of the present invention, a tissue cutter comprising a tissue cutting stent and a first reefing thread is provided. The tissue cutting stent is expandable in a radial direction. The expanded tissue cutting stent is loudspeaker-shaped gradually opening from a proximal end to a distal end, and a loudspeaker-shaped accommodating space is formed inside the expanded tissue cutting stent. The tissue cutting stent is provided with a plurality of first threading holes at the distal end. The plurality of first threading holes is arranged along a circumferential direction of the tissue cutting stent. The first reefing thread passes through the plurality of first threading holes and has opposite first and second ends. The first end is secured to a starting threading hole in the plurality of first threading holes.

Optionally, the tissue cutting stent comprises a fixed part, a support part and an expansion part. The fixed part, the support part and the expansion part are connected sequentially along the axial direction of the tissue cutting stent, from the proximal end to the distal end. The plurality of first threading holes is provided on the expansion part. The support part and the expansion part are expandable along the radial direction to form the accommodating space.

Optionally, the expansion part and the support part are in a web-like structure overall.

Optionally, the support part comprises a plurality of support segments provided along the circumferential direction of the tissue cutting stent. Each of the plurality of support segments has a root end and a tip end. The root end is connected to the fixed part and the tip end is connected to the expansion part.

Optionally, the expansion part has a single layer or multiple layers of annular structure. Each layer of annular structure comprises a plurality of expansion segments provided along the circumferential direction of the tissue cutting stent. Each expansion segment is V-shaped to make each expansion segment having two open ends and one pointed end. The open ends of adjacent two expansion segments in each layer of annular structure are connected.

In the case where the expansion part has a single layer of annular structure, the open ends are connected to the tip ends of the plurality of support segments in one-to-one correspondence, and the pointed end of each expansion segment is provided with one first threading hole.

In the case where the expansion part has multiple layers of annular structure, the multiple layers of annular structure are provided along the axial direction, wherein in adjacent two layers of annular structure, the open ends of one layer of annular structure and the pointed ends of the other layer of annular structure are connected in one-to-one correspondence; and wherein, the open ends of the layer of annular structure closest to the support segments are connected to the tip ends of the plurality of support segments in one-to-one correspondence, and the pointed ends of each expansion segment of the layer of annular structure farthest from the support segments are all provided with one first threading hole.

Optionally, each of the plurality of the support segments is rod-shaped, wherein in an expanded support part, the plurality of the support segments are radial from the root ends to the tip ends.

Optionally, in an expanded support part, each of the plurality of support segments is Y-shaped to make each of the plurality of support segments comprise one root end and two tip ends, wherein the root ends of the plurality of support segments are clustered with each other. In any adjacent two support segments, one tip end of one support segment is connected to one tip end of the other support segment.

Optionally, the pointed ends provided with the first threading holes rotate a predetermined angle in a plane perpendicular to the axial direction to make the first threading holes be at the predetermined angle to the radial direction of the tissue cutting stent.

Optionally, the expansion part gradually opens from its proximal end to its distal end.

Optionally, the expansion part bends radially outward with respect to the support part.

Optionally, the support part is provided with a plurality of second threading holes. The plurality of second threading holes is arranged along the circumferential direction of the tissue cutting stent. The tissue cutter further comprises a second reefing thread, which passes through the plurality of second threading holes.

Optionally, the second reefing thread sequentially passes through the plurality of second threading holes along the circumferential direction, and one end of the second reefing thread is secured to one of the plurality of second threading holes.

Optionally, the fixed part, the support part and the expansion part are formed by cutting a tubular product in the axial direction.

Optionally, the support part and the expansion part have a self-expending function.

Optionally, the proximal end of the tissue cutting stent has a center hole, which is communicated to the accommodating space along the axial direction. The second end of the first reefing thread passes out from inside the accommodating space via the center hole.

Optionally, the proximal end of the tissue cutting stent is further provided with a through-hole, which is communicated with the center hole.

Optionally, a middle section of the first reefing thread sequentially passes through the other threading holes in the plurality of first threading holes along the circumferential direction.

Optionally, the middle section of the first reefing thread passes through the other threading holes along the same direction.

Optionally, a middle section of the first reefing thread passes through the other threading holes in the plurality of first threading holes in a crisscross manner to make the first reefing thread form the web-like structure at the distal end of the tissue cutting stent.

Optionally, the tissue cutting stent further comprises a membrane, which covers the support part and the expansion part.

Optionally, the membrane comprises an inner layer and/or an outer layer. The inner layer covers the inner surfaces of the support part and the expansion part, and the outer layer covers the outer surfaces of the support part and the expansion part. The inner layer is an insulating layer, and the outer layer is an electrically conductive layer.

According to another aspect of the present disclosure, there is provided a minimally invasive interventional surgical instrument. The minimally invasive interventional surgical instrument comprises: the tissue cutting described above, a delivery sheath, a pusher and a connector. The contracted tissue cutting stent is accommodated within the delivery sheath, and the delivery sheath has a proximal opening at its proximal end and a distal opening at its distal end. The connector is connected between the pusher and the distal end of the tissue cutting stent. The pusher extends into the delivery sheath from the proximal opening of the delivery sheath to push the tissue cutting stent out from the distal opening of the delivery sheath.

Optionally, the connector comprises a plurality of elastic locking claws. The outer side of the proximal end of the tissue cutting stent is provided with a plurality of slots. Where the connector is located within the delivery sheath, the plurality of elastic locking claws are compressed along the radial direction, and the compressed plurality of elastic locking claws snap with the plurality of the slots, respectively. Where the plurality of the elastic locking claws is located outside the delivery sheath, the plurality of elastic locking claws are separated from the plurality of the slots along the radial direction.

Optionally, the first reefing thread and the tissue cutting stent are electrically conductive.

Optionally, the delivery sheath is electrically conductive, the outer surface of the tissue cutting stent is covered with an insulating outer layer, and the connector and the pusher are insulated from the delivery sheath.

Optionally, the distal end of the delivery sheath is provided with water-permeable holes, the tissue cutting stent is covered with a water-resisting membrane, and the space between the water-resisting membrane and the delivery sheath is communicated with the outside via the water-permeable holes.

Optionally, the minimally invasive interventional instrument further comprises a puncture needle, and the delivery sheath is accommodated within the puncture needle.

Optionally, the first reefing thread and the tissue cutting stent are electrically conductive, the puncture needle is electrically conductive, and the delivery sheath is insulating.

Optionally, at least one of the puncture needle, the delivery sheath and the first reefing thread is provided with scales.

Optionally, in the case where the fixed part is provided with a through-hole and the through-hole is communicated with the center hole, the minimally invasive interventional instrument further comprises a pneumatic device, which is used to inject air to the delivery sheath and/or extract air from the delivery sheath.

By using the tissue cutter provided by the embodiments of the present invention, the tissue cutter may be contracted into the delivery sheath before put into the human body, and the tissue cutter may self-expand or expand under the positive pressure exerted within the accommodating space after entering the human body. After the tissue resection is completed, the opening of the tissue cutter may be closed to wrap the tissues within it. The tissue cutter in the process of its closing may compress the wrapped tissues to a certain extent, so that only a minor incision is required to put the tissue cutter into the body or take the tissue cutter and the resected tissues out from the body. With tissues and organs like skin, muscle and fat having certain elasticity, in practice, it is possible to resect and take out the tissues larger than 10 mm in diameter via a skin incision of 2-3 mm. Such a minor incision may self-heal even without stitching. The advantage is that it is not needed to do general anesthesia for patients before the surgical procedure and both the surgical instrument and resection action in the present invention are simple to allow the completion of the surgery with imaging devices. In this way, it is possible to conduct accurate resection of lesioned tissues and achieve reduction of damages to the normal tissues and organs.

A series of concepts in simplified forms are introduced in the content of the invention, which will be described in further details in the section of specific embodiments. The content section of the present invention is not meant to attempt to define the key features and essential technical features of the technical solution claimed to be protected, much less to attempt to determine the scope of protection of the technical solution claimed to be protected.

The advantages and features of the present invention are described in detail below in conjunction with the drawings.

BRIEF DESCRIPTION OF THE DRAWINGS

The following drawings of the present invention are used herein as a part of the present invention for the purpose of understanding the present invention. The embodiments of the present invention and descriptions thereof are shown by the drawings for explaining the principles of the present invention. In the drawings.

Wherein, the aforesaid drawings include the following signs;

1, 1', 1", tissue cutting stent; 2, puncture needle; 3, delivery sheath; 4, 4', connector; 5, first reefing thread; 6, pusher; 7, second reefing thread; 10, fixed part; 12, center hole; 14, through-hole; 16, opening; 18, slot; 20, 20', 20", support part; 200, 200', support segment; 210, root end; 220, 220', tip end; 22, first support segment; 24, second support segment; 242, second left support segment; 244, second right support segment; 30, 30', 30", expansion part; 310, 310', open end; 320, 320', pointed end; 32, left expansion segment; 34, right expansion segment; 40, accommodating space; 42, snap clip; 44, elastic locking claw; 50, 50', first threading hole; 52, starting threading hole; 60, outer layer; 70, second threading hole.

DETAILED DESCRIPTION OF THE EMBODIMENTS

In the following descriptions, a lot of details are provided to enable a thorough understanding of the present invention. However, it can be understood by those skilled in the art that the following descriptions only exemplarily illustrate preferred embodiments of the present invention, and that the present invention can be implemented without one or more of such details. Furthermore, in order to avoid confusion with the present invention, some technical features well known in the art are not described in detail.

In order to solve the problem of minimally invasive resection of the lesions in tissues and organs (rather than cavities such as blood vessel or trachea), the present invention provides a tissue cutter and a minimally invasive interventional surgical instrument. The tissue cutter comprises a tissue cutting stent which can be inserted into tissues and organs after contraction, spread therein and resect the lesioned tissues while advancing therein, and after resection, be closed to wrap the resected tissues and take out the tissues from the body. The minimally invasive interventional instrument includes the tissue cutter. In order to overall understand the present invention, the minimally invasive interventional instrument will first be described in detail below.

Figure 1:
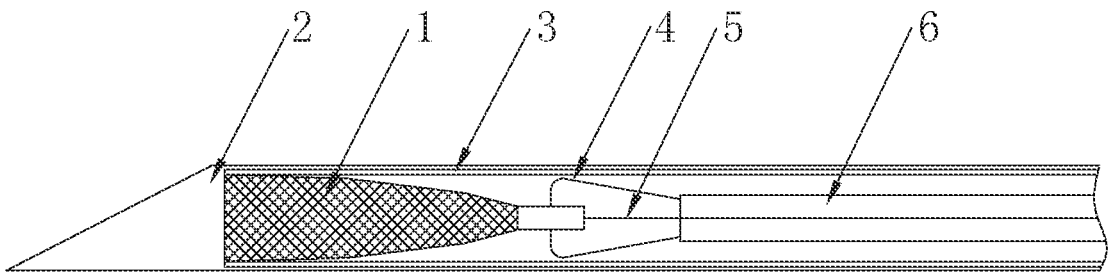
FIG. 1 is a schematic diagram of a minimally invasive interventional surgical instrument according to one embodiment of the present invention, wherein the tissue cutting stent is in a contracted state.
Figure 2:
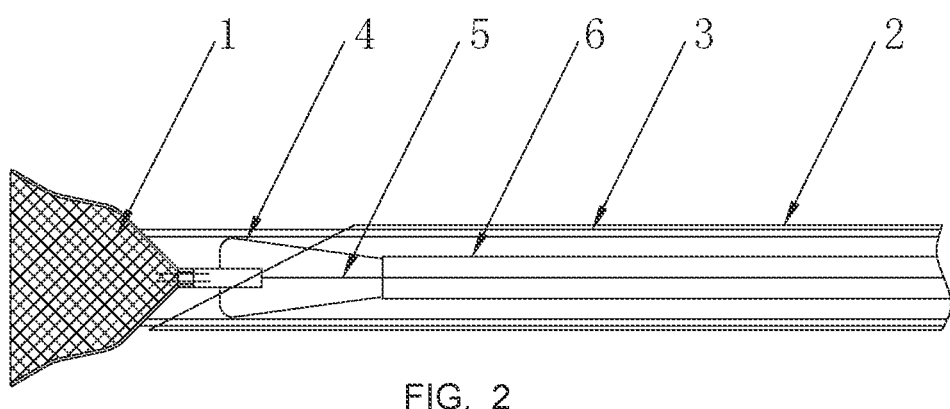
FIG. 2 is a schematic diagram of the minimally invasive interventional surgical instrument of FIG. 1, wherein the tissue cutting stent is in an expanded state.
Figure 3:
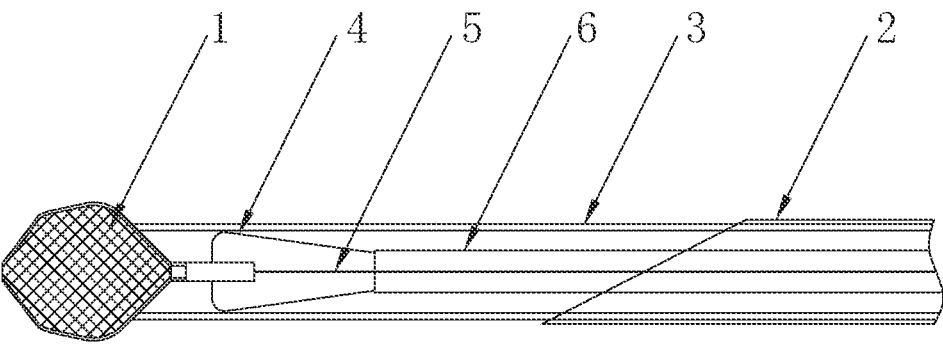
FIG. 3 is a schematic diagram of the minimally invasive interventional surgical instrument of FIG. 1, wherein the tissue cutting stent is in a closed state.

FIGS. 1-3 illustrate three states of a minimally invasive interventional surgical instrument according to an exemplary embodiment of the present invention. The minimally invasive interventional surgical instrument comprises a tissue cutter, a delivery sheath 3, a pusher 6, and a connector 4. In one embodiment, the tissue cutter may comprise a tissue cutting stent 1 and a first reefing thread 5.

The contracted tissue cutting stent 1 is accommodated within the delivery sheath 3. The delivery sheath 3 has a proximal opening at its proximal end and a distal opening at its distal end. The delivery sheath 3 may be tube-shaped. The delivery sheath 3 may penetrate the body of a patient along the axial direction of the tube, and the openings at the both ends of the tube form the proximal opening and the distal opening, respectively. The terms "proximal" and "distal" herein are relative to the surgeon performing the minimally invasive interventional surgery with the minimally invasive interventional instrument, wherein the proximal end is close to the surgeon and the distal end is away from the surgeon.

The connector 4 is connected between the pusher 6 and the tissue cutting stent 1. The connector 4 may be connected to the tissue cutting stent 1 in a detachable, non-detachable, self-releasable manner and so on, more specifically to the proximal end of the tissue cutting stent 1 which will be described in detail below. The detachable connection includes snap connection, threaded connection, pin insertion and so on. The beneficial effect of the detachable connection is that the tissue cutting stent 1 can be disassembled from the connector 4 after the use, and only the tissue cutting stent 1 is required to be replaced each time for use. The non-detachable connection includes welding, bonding, interference fit and so on. The self-releasable connection means that the connector 4 can be self-released from the tissue cutting stent 1 when a constraint force on the connector 4 is removed. The constraint force may be a radial restraining force exerted on it by the delivery sheath 3. The constraint force is removed when the connector 4 is pushed out of the delivery sheath 3, thereby allowing the connector 4 to be released from the tissue cutting stent 1. The self-releasable connection is suitable for the case where the tissue cutting stent 1 remains in the body after resecting and wrapping the lesioned tissues which can be subsequently found and taken out along the first reefing thread 5 by a surgery, or degrade spontaneously after long-term implantation as needed.

The pusher 6 extends into the delivery sheath 3 from the proximal opening of the delivery sheath 3, and is used to push the tissue cutting stent 1 out from the distal opening of the delivery sheath 3. By the pusher 6, the tissue cutting stent 1 may be pushed completely or partially out of the delivery sheath 3 via the distal opening. Those skilled in the art can make a reasonable choice depending on the needs of the surgical procedure. In an embodiment where the connector 4 is connected to the tissue cutting stent 1 in the self-releasable manner, the pusher 6 may also push a portion or whole of the connector 4 out of the body.

Figure 4A:
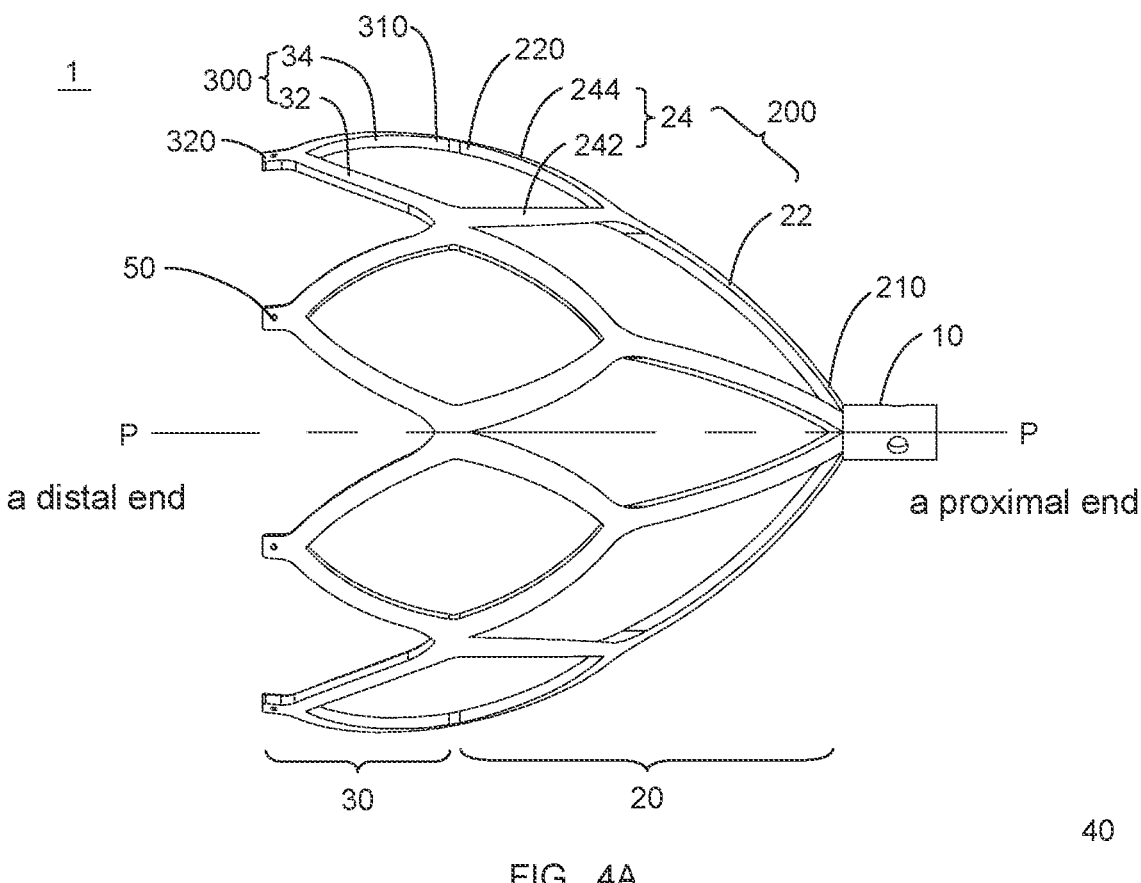
FIGS. 4A-4C are schematic diagrams of a tissue cutting stent from different angles according to one exemplary embodiment of the present invention, respectively, wherein the tissue cutting stent is in an expanded state.
Figure 4B:
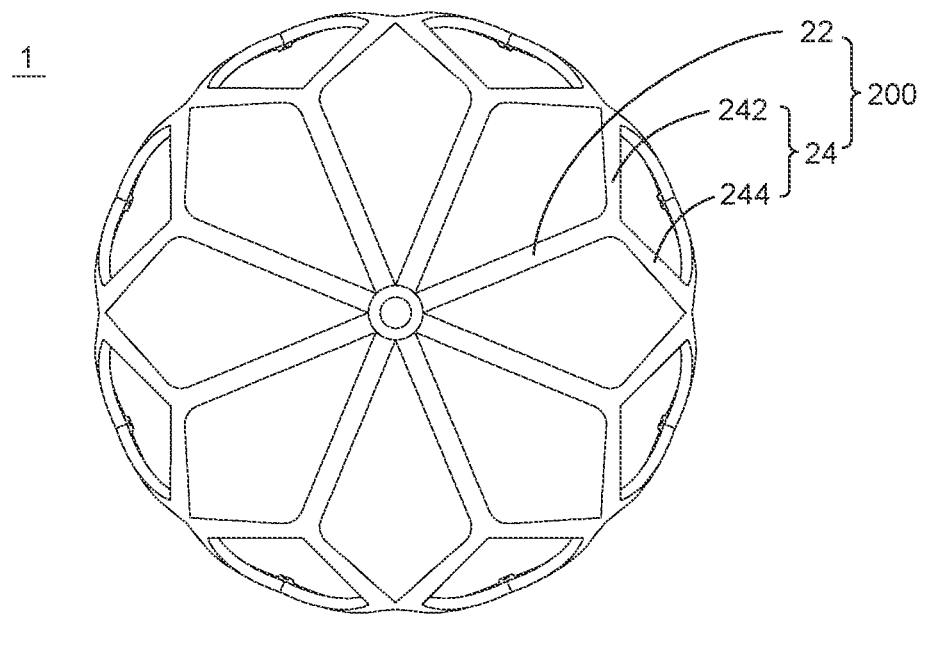
Figure 4C:
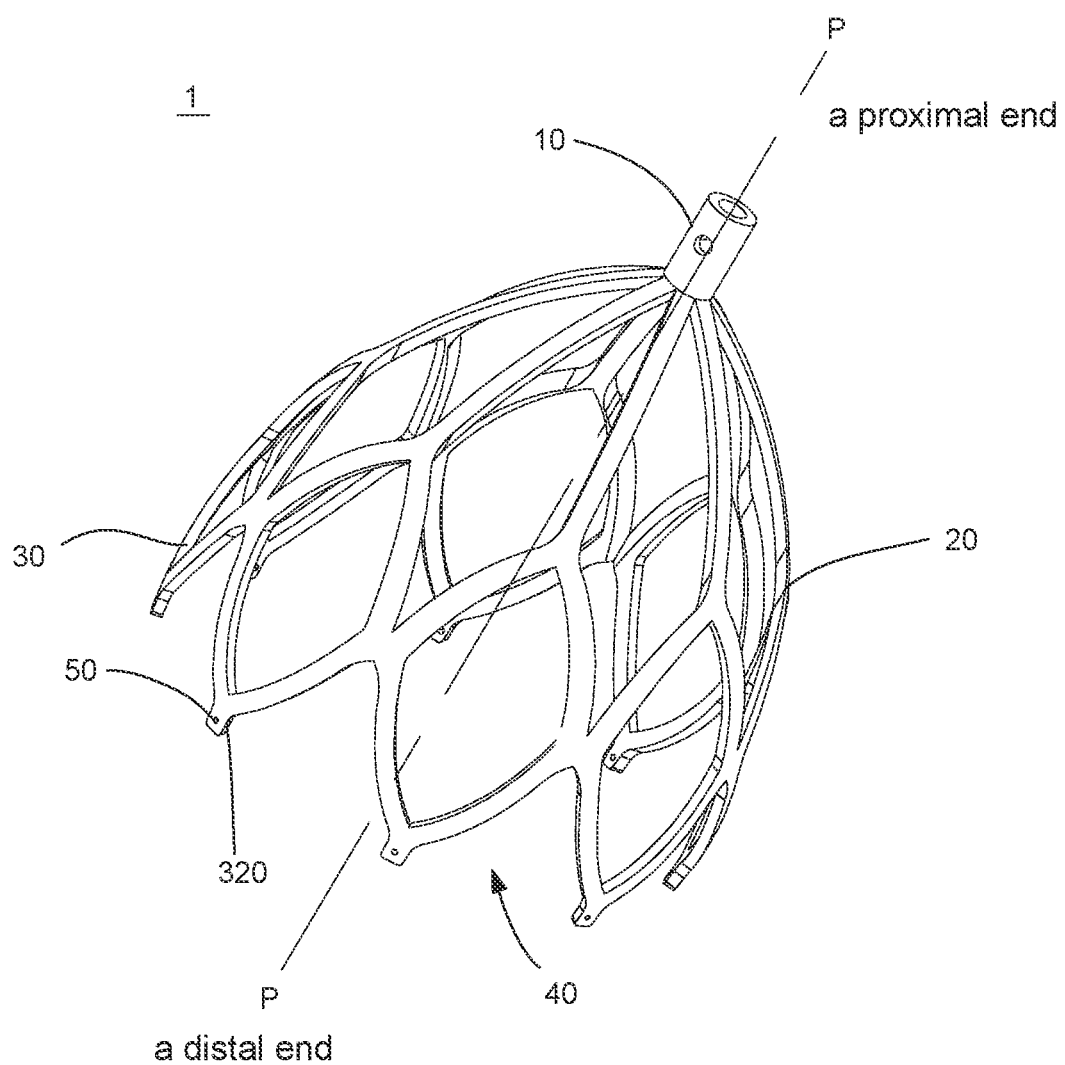
Figure 5:
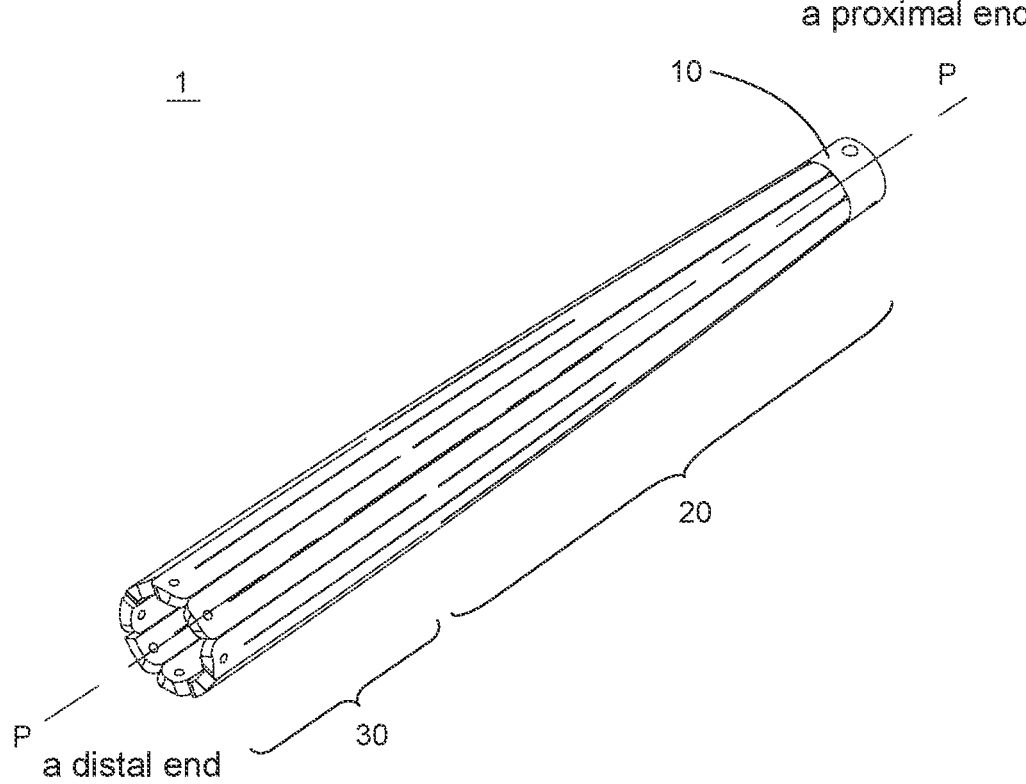
FIG. 5 is a schematic diagram of the tissue cutting stent of FIG. 4, wherein the tissue cutting stent is in a contracted state.

FIGS. 4A-4C and FIG. 5 all illustrate a tissue cutting stent 1 according to an exemplary embodiment of the present invention, wherein the tissue cutting stent 1 in FIGS. 4A-4C is in an expanded state and the tissue cutting stent 1 in FIG. 5 is in a contracted state.

The tissue cutting stent 1 is expandable in the radial direction. The expanded tissue cutting stent 1 is loudspeaker-shaped gradually opening from the proximal end to the distal end. The expanded tissue cutting stent 1 forms a loudspeaker-shaped accommodating space 40. The accommodating space 40 is used to accommodate the resected tissue. The tissue cutting stent 1 before expansion may be elongated, which facilitates to be accommodated within the delivery sheath 3. The tissue cutting stent 1 is provided with a plurality of first threading holes 50 at the distal end thereof. The plurality of first threading holes 50 are arranged along the circumferential direction of the tissue cutting stent 1. The first reefing thread 5 passes through the plurality of first threading holes 50. The first reefing thread 5 has opposite first and second ends, and the first end thereof is secured to one of the plurality of first threading holes 50. The second end thereof may be used for tighten the opening of the tissue cutting stent 1 by being lifted.

In a specific embodiment, as shown in the drawings, the tissue cutting stent 1 may include a fixed part 10, a support part 20, and an expansion part 30.

The fixed part 10, the support part 20 and the expansion part 30 are arranged sequentially along the axial direction of the tissue cutting stent 1 (i.e., the extension direction of the axis P-P as shown in the drawings). In use, the fixed part 10 is located at the proximal end of the tissue cutting stent 1, and the expansion part 30 is located at the distal end of the tissue cutting stent 1. The support part 20 is connected between the fixed part 10 and the expansion part 30. The proximal end of the support part 20 is connected to the fixed part 10. The proximal end of the expansion part 30 is connected to the distal end of the support part 20.

The expansion part 30 and the support part 20 are expandable along the radial direction. The fixed part 10 does not have an expansion function, and accordingly under the constraint of the fixed part 10, the expanded expansion part 30 and the support part 20 are loudspeaker-shaped gradually opening from the proximal end to the distal end. Preferably, the ratio of the outer diameter of the distal end of the loudspeaker to the outer diameter of the proximal end thereof is greater than 5:1. The expanded expansion part 30 and the support part 20 together form the loudspeaker-shaped accommodating space 40.

Exemplarily, the expansion part 30 and the support part 20 may be made of any material having expansion and contraction capacities, such as an elastic material. The expansion part 30 and the support part 20, when not subject to an external force, are loudspeaker-shaped. When subject to a radially inward pressure, the elastic material can be compressed, thus the expansion part 30 and the support part 20 can be contracted to the shape as shown in FIG. 5, thereby accommodated within the delivery sheath 3.

Exemplarily, the expansion part 30 and the support part 20 are in a web-like structure overall. Even though the material itself, which forms the web-like structure, may not be elastic, the web-like structure may allow the expansion part 30 and the support part 20 to expand and contract. In this case, optionally, the expansion part 30 and the support part 20 may be made of a shape-memory material (such as, a memory alloy). The expansion part 30 and the support part 20, when not subject to an external force, are loudspeaker-shaped. When subject to a radially inward pressure, the expansion part 30 and the support part 20 may be contracted to the shape as shown in FIG. 5, thereby accommodated within the delivery sheath 3. Optionally, the expansion part 30 and the support part 20 may be made of a deformable material. After the tissue cutting stent 1 is placed into the human body, a positive pressure may be exerted within the accommodating space 40, such as inflating the accommodating space 40 or injecting liquid to the accommodating space 40, to make the expansion part 30 and the support part 20 expand. Of course, the expansion part 30 and the support part 20 may also be of the web-like structure made of the elastic material. Only one style web-like structure is shown in FIGS. 4A-4C, and in the other embodiments not shown, the web-like structure may have other styles as long as its function can be realized.

In the case where the expansion part 30 and the support part 20 are made of the elastic material or the shape-memory material, the expansion part 30 and the support part 20 may have a self-expanding function. Of course, the expansion part 30 and the support part 20 may not have the self-expanding function, but expands to a desired shape by an external force (such as a positive pressure to be described below) after being pushed out of the delivery sheath 3. These two sets of embodiments respectively have their own benefits. The expansion part 30 and the support part 20 with the self-expanding function automatically expand to a desired shape after being pushed out of the delivery sheath 3, making the surgeon's operation relatively simple. In the embodiments where the external force is required to force the expansion part 30 and the support part 20 to expand after being pushed out of the delivery sheath 3, the external force can help the tissue cutting stent expand in more dense tissues and organs (such as dense breast, prostate and so on).

The plurality of threading holes 50 may be provided at the distal end of the expansion part 30. Optionally, the plurality of threading holes 50 may be provided uniformly along the circumferential direction of the expansion part 30 at its distal end. Optionally, the plurality of threading holes 50 may also be provided at unequal intervals.

Figure 6A:
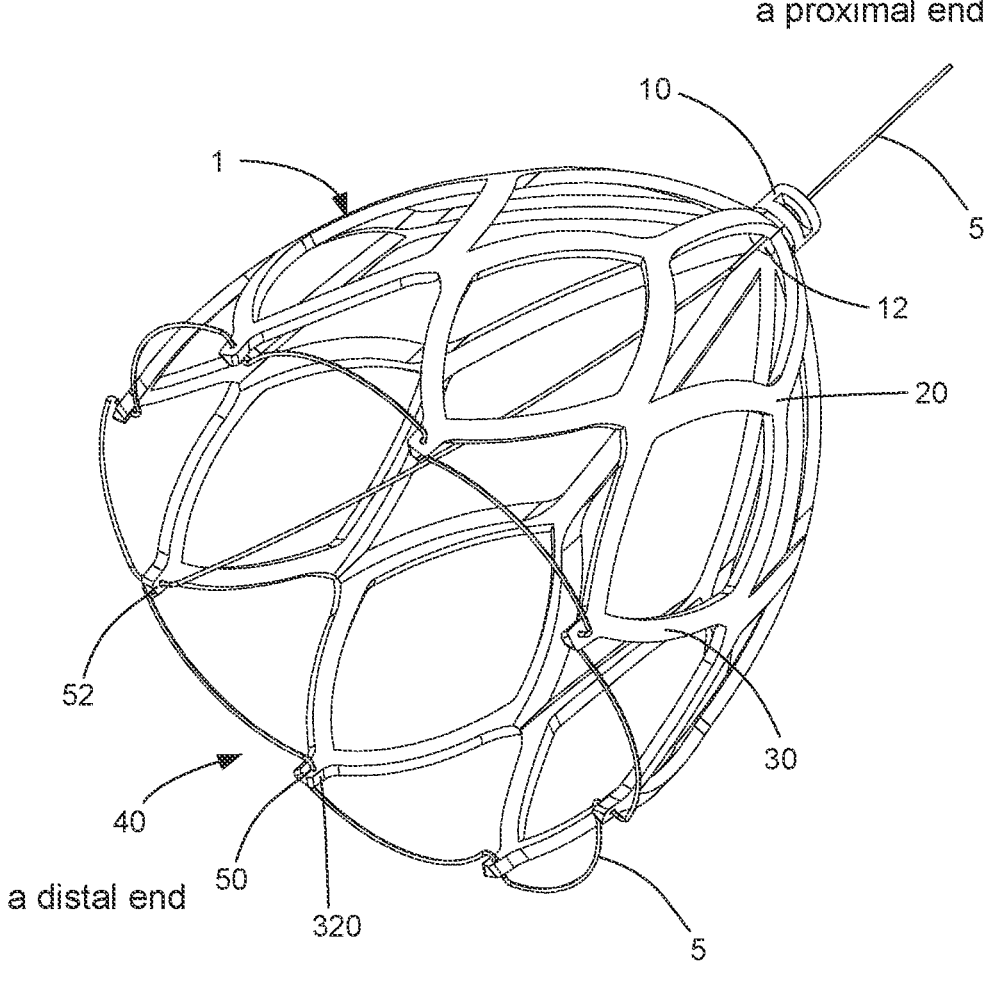
FIGS. 6A-6B are schematic diagrams of a tissue cutter from different angles according to the first exemplary embodiment of the present invention, respectively, wherein the first reefing thread is in a Z-shaped threading manner.
Figure 6B:
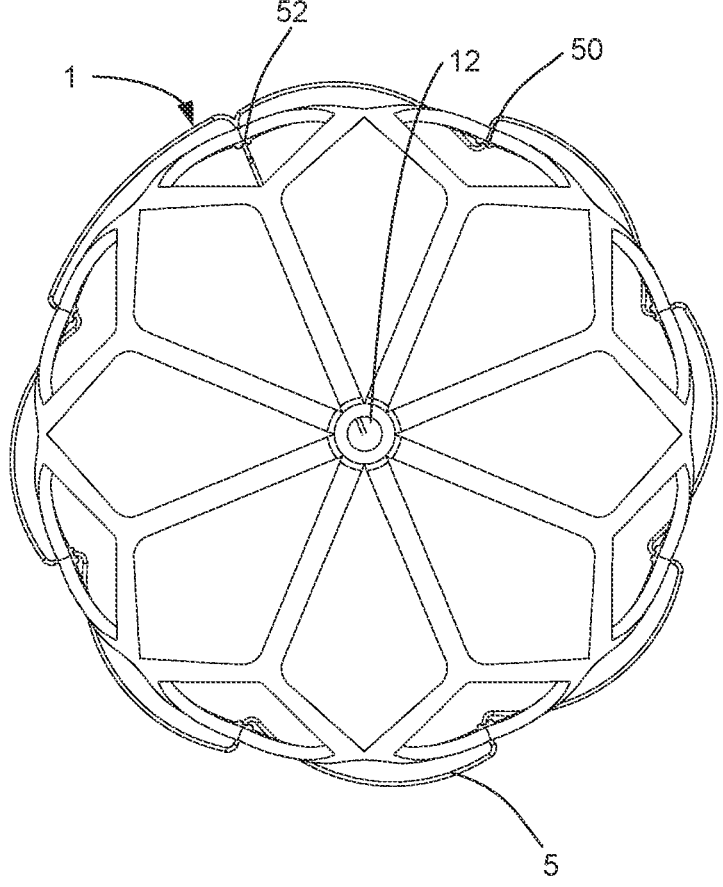
Figure 7:
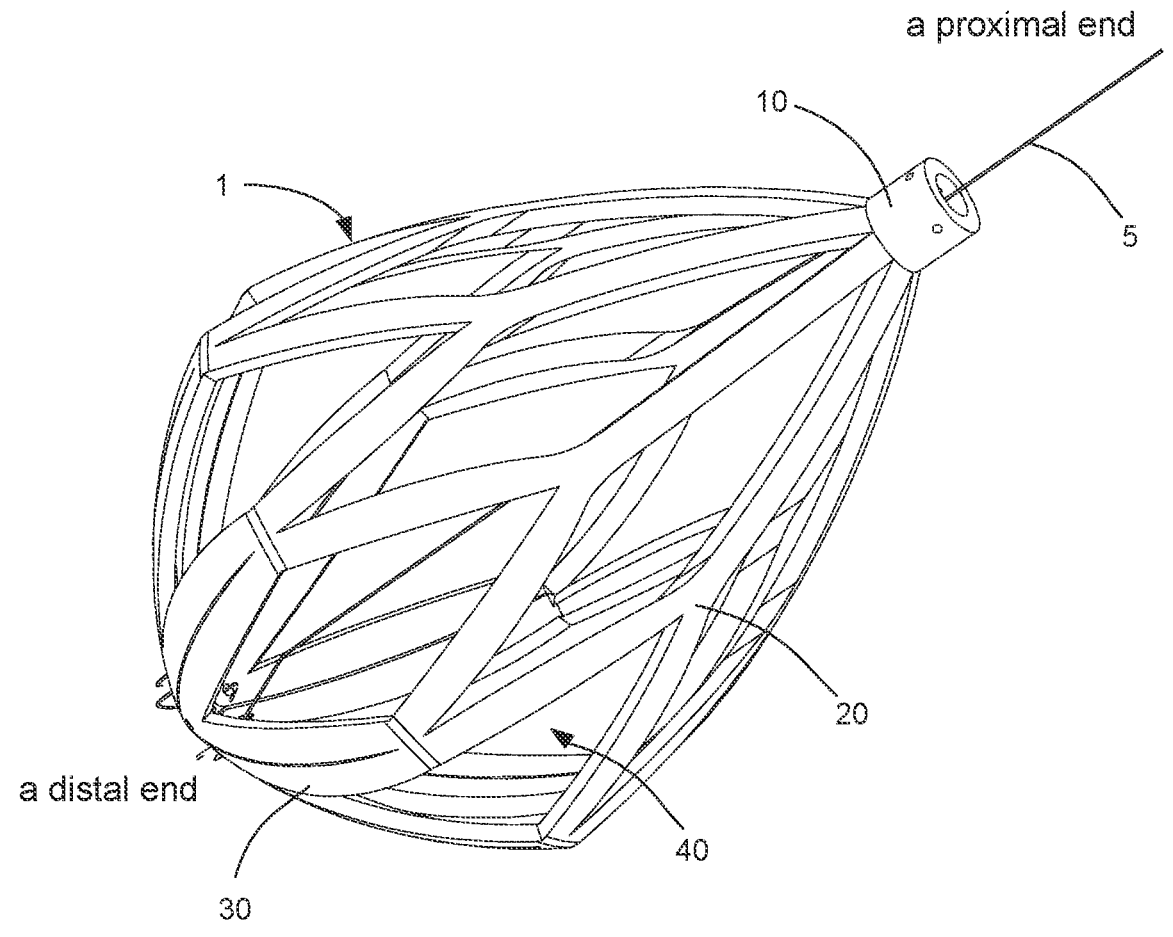
FIG. 7 is a schematic diagram of the tissue cutter according to the first exemplary embodiment of the present invention, wherein the tissue cutting stent is in a closed state.

The fixed part 10 is used to connect to the pusher 6. The fixed part 10 may have a center hole 12. Preferably, the center hole 12 may pass through the fixed part 10 along the axial direction. The center hole 12 is communicated with the accommodating space 40. The first reefing thread 5 may extend into the accommodating space 40 through the center hole 12, wherein the section of the first reefing thread 5 extending into the accommodating space 40 passes through the plurality of threading holes 50, as shown in FIGS. 6A-6B. During the surgeon pulls a second end of the first reefing thread 5 at the proximal end, the distal end of the expansion part 30 gradually close, thereby wrapping the tissues that have entered into the accommodating space 40, as shown in FIGS. 3 and 7. The surgeon may take them out immediately, or leave them temporarily in the body, or allow them to degrade spontaneously after long-term implantation as needed. Optionally, the fixed part 10 may not be provided with the center hole 12. The first reefing thread 5 may extend into the accommodating space 40 from a position of the support part 20 close to the fixed part 10.

By using the tissue cutter provided by the embodiments of the present invention, the tissue cutter may be contracted into the delivery sheath 3 before put into the human body, and be pushed out of the delivery sheath 3 by the pusher 6 after entering the human body. The tissue cutter after being pushed out may self-expand or expand under the positive pressure exerted within the accommodating space 40. Thus, the delivery sheath 3 may have a very small diameter to put the tissue cutter into the human body. After the tissue resection is completed, the opening of the tissue cutter may be closed by the first reefing thread to wrap the tissues within it. The tissue cutter in the process of its closing may compress the wrapped tissues to a certain extent, so that only a minor incision is required to take the tissue cutter and the resected tissues out. With tissues and organs like skin, muscle and fat having certain elasticity, in practice, it is possible to resect and take out the tissues larger than 10 mm in diameter via a skin incision of 2-3 mm. Such a minor incision may self-heal even without stitching. The advantage is that it is not needed to do general anesthesia for patients before the surgical procedure and as compared to thoracoscopy or laparoscopy, both the surgical instrument and resection action in the present invention are simple to allow the completion of the surgery with imaging devices. In this way, it is possible to conduct accurate resection of lesioned tissues and achieve reduction of damages to the normal tissues and organs.

To sum up, by using the tissue cutter provided in the present invention to perform the minimally invasive surgery for resecting lesioned tissues, because of the minor incision created on the body surface and the target tissues and organs of the human, and accurate resection of only lesioned tissues, more normal tissues and organs are kept, the damages caused to patients are less, their recovery is faster and their long-term quality of life can be ensured.

Exemplarily, the support part 20 comprises a plurality of support segments 200, and the support segments 200 are provided along the circumferential direction of the tissue cutting stent 1. Each of the support segments 200 has a root end 210 and a tip end 220. The root end 210 is connected to the fixed part 10. The tip end 220 is connected to the expansion part 30.

In a preferred embodiment, each support segment 200 is Y-shaped, thus each support segment comprises one root end 210 and two tip ends 220, referring to FIGS. 4A-4B. In the expanded support part, the root ends 210 of the plurality of support segments 200 are clustered with each other, and in any two adjacent support segments, one tip end 220 of one support segment is connected to one tip end 220 of the other support segment.

That is, each support segment 200 may comprise one first support segment 22 and a pair of second support segments 24. Thus, for the expanded support part 20, a plurality of first support segments 22 are radial along a direction from the proximal end to the distal end. The angle between adjacent first support segments 22 may be equal or unequal. The proximal ends of the plurality of first support segments 22 are connected to the fixed part 10. The distal ends of the plurality of first support segments 22 are connected to the second supports 24. For clear description below, a pair of second support segments 24 comprised in each support segment 200 are called as second left support segment 242 and second right support segment 244, respectively. For any adjacent two support segments 200, the second left support segment 242 of one support segment 200 is connected to the second right support segment 244 of the other support segment 200 at the tip end 220. That is, for each pair of second support segments 24, the second left support segment 242 therein and the second right support segment 244 of the left-side adjacent support segment 200 are connected to each other at the tip end 220, while the second right support segment 244 therein and the second left support segment 242 of the right-side adjacent the support segment 200 are connected to each other at the tip end 220. Accordingly, the expanded support part 20 diverges in a tree-like manner along the direction from the proximal end to the distal end.

In this way, on the basis of ensuring that the support part 20 has sufficient and uniform radial support strength, the axial length of the support segment 200 can be extended, which in turn can make the tissue cutting stent 1 have large enough radial dimension and accommodating space so as to resect a sufficient number of lesioned tissues each time. And, the support part 20 may have more uniformly dimensioned meshes along the axial direction to avoid the tissues wrapped within it from penetrating outside the support part 20 via the larger meshes, resulting in that the radial dimension of the support part 20 in the closed state is not uniform at each position.

Figure 10A:
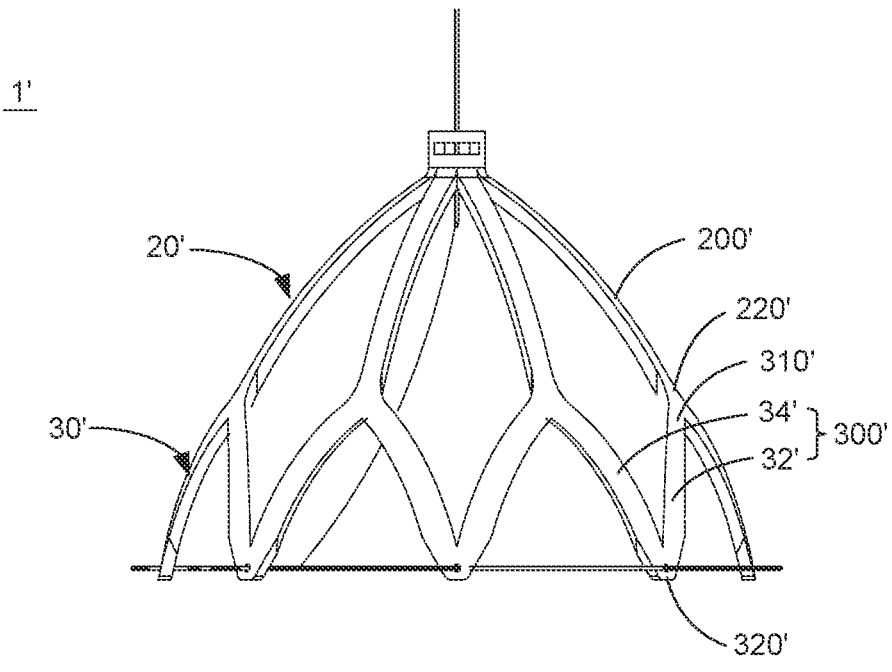
FIGS. 10A-10B are schematic diagrams of a tissue cutter from multiple angles according to the fourth exemplary embodiment of the present invention, respectively.
Figure 10B:
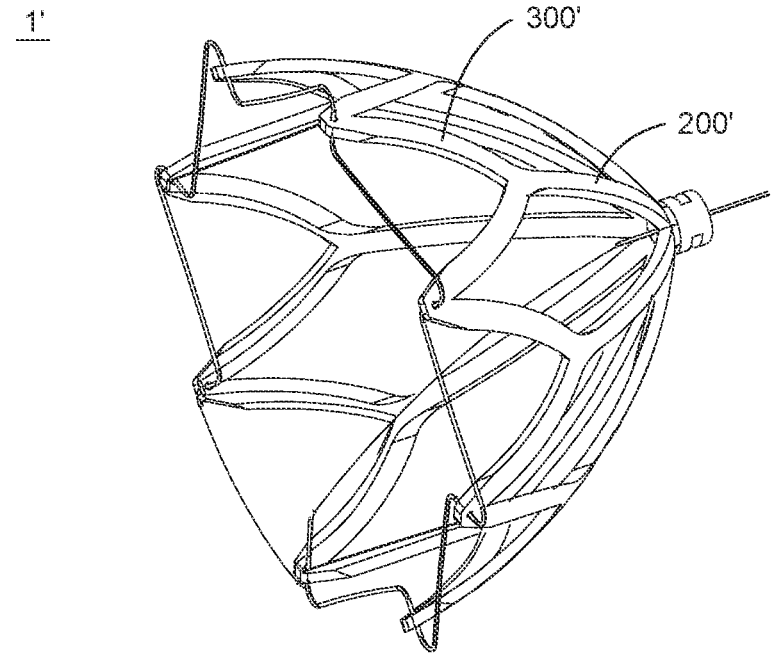

In another preferred embodiment, each of the plurality of support segments 200' is rod-shaped, as shown in FIGS. 10A-10B. In the expanded support part 20', the plurality of support segments 200' are radial from the root ends to the tip ends as if an umbrella bone. Under the premise that the expansion diameter of the tissue cutting stent is unchanged, in this scheme, the axial dimension of the expanded stent is shortened, the volume of the accommodating space 42 is reduced and the number of tissues that can be resected in once time is decreased, but at the same time, the axial dimension of the contracted tissue cutting stent 1' can be shortened and the release distance of the stent be reduced (the distance between the delivery sheath and the target lesions before the release of the stent), which is suitable for the case where the lesions are closer to the edge of the tissues and organs. The surgeon may choose an appropriate tissue cutting stent as needed.

Exemplarily, the expansion part may have a single layer or multiple layers of annular structure. Each layer of annular structure comprises a plurality of expansion segments, and the plurality of expansion segments are provided along the circumferential direction of the tissue cutting stent. Each expansion segment is V-shaped, so that each expansion segment has two open ends and one pointed end. The open ends of adjacent two expansion segments in each layer of annular structure are connected.

Back to see FIGS. 4A-4C, the expansion part 30 has a single layer of annular structure. The expansion part 30 comprises a plurality of expansion segments 300. The expansion segments 300 are V-shaped with the opening thereof facing the proximal end, that is, two open ends 310 of each expansion segment 300 are located at the proximal end of the expansion segment 300 and one pointed end 320 of each expansion segment 300 is located at the distal end of the expansion segment 300. For clear description below, the two sides of the V-shape are noted as left expansion segment 32 and right expansion segment 34, respectively. The left expansion segment 32 and the right expansion segment 34 are connected to each other at the distal end to form the pointed end 320. The proximal ends of the left expansion segment 32 and the right expansion segment 34 are spaced apart from each other to form two open ends 310, but the open ends 310 of adjacent two expansion segments 300 are connected to each other to form the ring structure. And, the open ends 310 are connected to the tip ends 220 of the plurality of support segments 200 in one-to-one correspondence.

In the illustrated embodiments, for each pair of the second support segments 24, the second left support segment 242 therein is connected to the left expansion segment 32, and the second right support segment 244 therein is connected to the right expansion segment 34. Thereby, a pair of second support segments (i.e., the second left support segment 242 and the second right support segment 244) and a pair of expansion segments (i.e., the left expansion segment 32 and the right expansion segment 34) are connected to form a small ring. Along the circumferential direction of the tissue cutting stent 1, adjacent small rings are connected to each other to form a large ring. In this way, a stable structure can be obtained.

The pointed end 320 of each expansion section 300 is provided with one first threading hole 50. Thereby, the threading holes 50 may be uniformly distributed at the distal end of the expansion part 30. With the first reeling thread 5 passing through the threading holes 50, as shown in FIG. 6A, when the surgeon pulls the first reefing thread 5, the first reefing thread 5 firstly draws the distal end of the expansion part 30 inward. With the first reefing thread 5 being completely pulled tight, the distal end of the expansion part 30 is completely closed, as shown in FIG. 7, thereby the resected tissues can be wrapped within the accommodating space 40.

In the embodiments as shown in FIGS. 10A-10B, since each support segment 200' has only one tip end 220', two open ends 310' of each expansion segment 300' are respectively connected to two support segments 200', while each support segment 200' is connected to one of the open ends 310' of adjacent two expansion segments 300', respectively.

Although not shown in the drawings, according to the disclosures of the present invention, those skilled in the art may conceive that in the case where the expansion part 30 and 30' has multiple layers of annular structure, the multiple layers of annular structures may be provided in the axial direction. That is, in adjacent two layers of annular structure, the open ends of one layer of annular structure and the pointed ends of the other layer of annular structure are connected in one-to-one correspondence. For the embodiment as shown in FIGS. 10A-10B, if one more layer of annular structure is added, it can be considered that two pointed ends of each expansion segment comprised in the added layer of annular structure are connected to two pointed ends 320' of two expansion segments 300', respectively. Of course, more layers of annular structure may be added. Wherein, the open ends 310' of the layer of annular structure closest to the support segments 200' are connected to the tip ends 220' of the plurality of support segments 200' in one-to-one correspondence, and the pointed end of each expansion segment of the layer of annular structure farthest from the support segments 200' is provided with one first threading hole. It should be noted that the expansion part of the multiple layers of annular structure may also be combined with the support part with the Y-shaped support segments.

Exemplarily, the expansion part 30 and the support part 20 have a thinner thickness along the radial direction of the tissue cutting stent 1, thus the expansion part 30 and the support part 20 can expand and contract along the radial direction. The width of the expansion part 30 and the support part 20 is somewhat greater than the thickness thereof. The width here refers to the dimension of each expansion segment 300 of the expansion part 30 as well as that of each first support segment 22 and second support segment 24 of the support part 20 along the circumferential direction of the tissue cutting stent 1. Accordingly, the threading holes 50 extend along the radial direction of the tissue cutting stent 1, as shown in FIGS. 6A-6B, more beneficial to ensure the adequate mechanical strength of the pointed ends 320 provided with the threading holes 50.

In a preferred embodiment, the fixed part 10, the support part 20 and the expansion part 30 are formed by cutting a tubular product in the axial direction. The tubular product may have a thinner wall. The formation of the tissue cutting stent 1 by cutting the tubular product is critical for the following reasons: the thin stent structure formed by cutting the tubular product provides not only the strongest radial bracing force but also sufficient rigidity to ensure that the tissue cutting stent 1 does not twist while it advances within the tissues and organs, thus enabling smooth expansion to a predetermined dimension in solid organs. In addition, an integrated stent structure ensures minimal outer diameter of the entire stent after contraction, reducing the risk of puncture; and it is more suitable for maintaining the shape while advancing in solid organs with resistance. This is something that cannot be achieved with a web-like woven structure or a rod-shaped expansion structure. Of course, the present invention does not exclude embodiments where the web-like structure of the support part 20 and the expansion part 30 is a web-like woven structure or a rod-shaped expansion structure.

As previously described, the first end of the first reefing thread 5 may be secured to the starting threading hole 52 in the plurality of threading holes 50. After passing through the other threading holes, the first end may extend from inside the accommodating space 40 via the center hole 12 on the fixed part 10 to the outside of the body. The first reefing thread 5 is connected to all the other threading holes in a manner of sliding connection. After the surgeon pulls the first reefing thread 5 outside the body to close the tissue cutting stent 1, the first reefing thread 5 remains connected to the tissue cutting stent 1.

In addition, the first reefing thread 5 may be threaded through the tissue cutting stent 1 in various manners.

In a preferred embodiment, the first reeling thread 5 adopts a Z-shaped threading manner. As shown in FIGS. 6A-6B, the first end of the first reefing thread 5 is secured to the starting threading hole 52, and the middle section of the first reefing thread 5 sequentially passes through the other threading holes along the circumferential direction. Preferably, the middle section of the first reefing thread 5 passes through the other threading holes in the same direction. In this way, when the tissue cutting stent 1 is in the closed state, adjacent two first threading holes 50, because of the effect of the first reefing thread 5, may not fit perfectly along the circumferential direction of the tissue cutting stent 1, and also have a tendency to be separated from each other along the radial direction. For example, in the case of passing through the other threading holes sequentially from the inside to the outside, the next threading hole tends to be located radially outside the previous threading hole, and the two are spaced apart along the circumferential direction, thereby the first reefing thread 5 when tightening has a plurality of bends at the plurality of first threading holes 50, so that it has certain self-locking effect, and accordingly the tissue cutting stent 1 is not likely to expand easily.

Figure 8A:
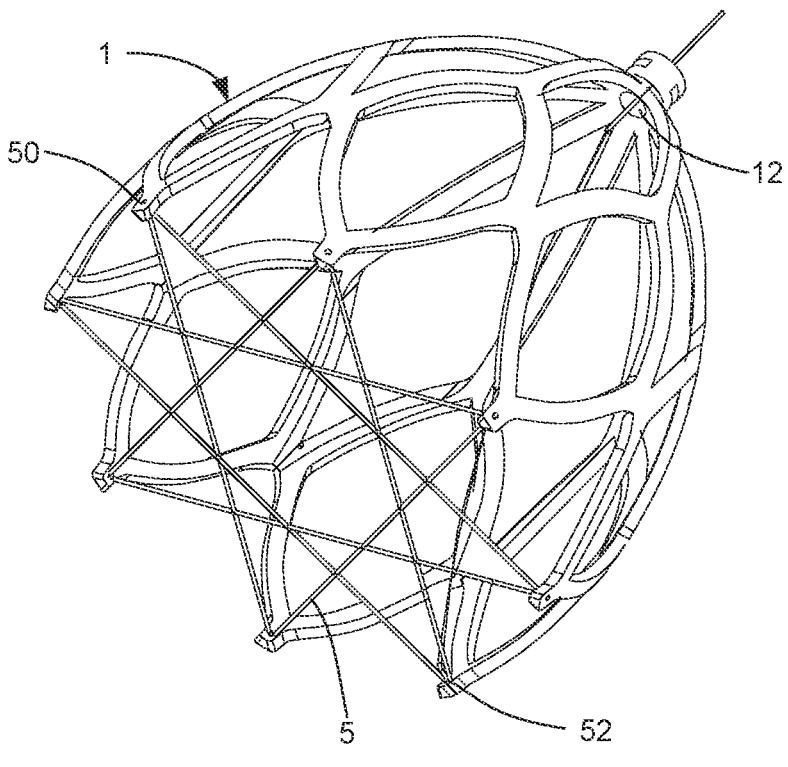
FIGS. 8A-8B are schematic diagrams of a tissue cutter from different angles according to the second exemplary embodiment of the present invention, respectively, wherein the first reefing thread is in a star-shaped threading manner.
Figure 8B:
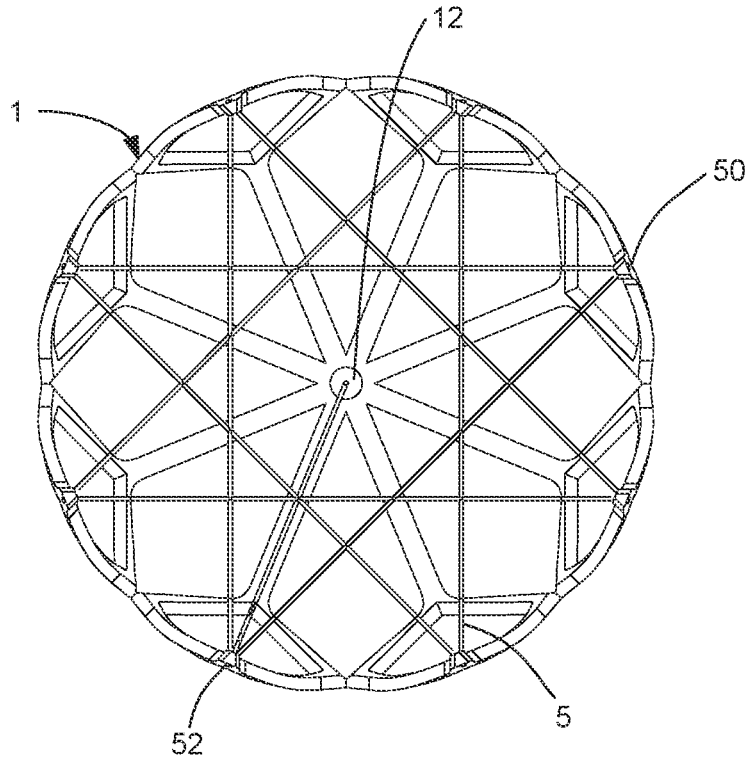

In another preferred embodiment, after the first end of the first reefing thread 5 passes through the starting threading hole 52, the middle section of the first reefing thread 5 passes through the other threading holes in a crisscross manner, so that the first reefing thread 5 forms a web-like structure at the distal end of the tissue cutting stent 1. As shown in FIGS. 8A-8B, one threading matter of the first reefing thread 5 to form the web-like structure is illustrated. In other embodiments not shown, the first reefing thread 5 may adopt other threading matters as long as a web-like structure can be formed. The advantage of this threading manner is that the web-like first reefing thread 5 at the front end can have the function of resecting the lesioned tissues while the tissue cutting stent 1 advances within the tissues and organs, facilitating to shatter the lesioned tissues. Therefore, those skilled in the art can set the mesh dimension of the web-like structure as needed to obtain the lesioned tissues in a desired degree of shattering. After shattering the tissues, the shattered tissues are wrapped in the tissue cutting stent 1, which facilitates the tissues to be compressed smaller after the tissue cutting stent 1 is closed, thereby further ensuring that the incision has a smaller dimension.

Figures 9A, 9B:
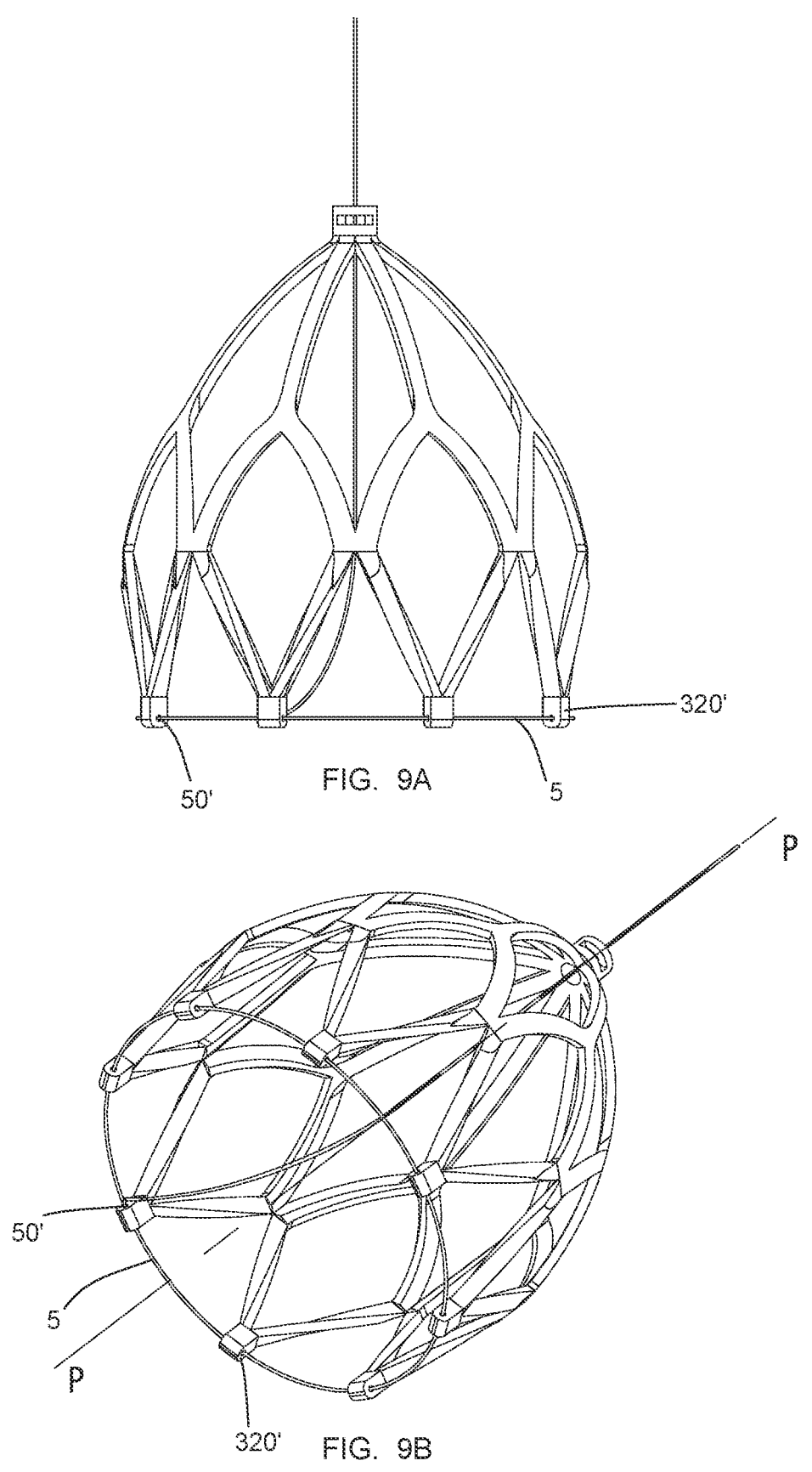
FIGS. 9A-9B are schematic diagrams of a tissue cutter from different angles according to the third exemplary embodiment of the present invention, respectively, wherein the first reefing thread is in an annular threading manner.

In a further preferred embodiment, as shown in FIGS. 9A-9B, the pointed ends 320' of the expansion segments rotates by a predetermined angle in a plane perpendicular to the axial direction P-P of the tissue cutting stent 1 with respect to the pointed ends 320 in the preceding embodiment, to make the first threading holes 50' on the pointed ends 320' at the predetermined angle to the radial direction of the tissue cutting stent 1. In the preceding embodiment, the first threading holes 50 on the pointed ends 320 extend along the radial direction of the tissue cutting stent 1. With the rotation of the pointed ends 320' in the plane perpendicular to the axis P-P, the first threading holes 50' thereon rotate accordingly, and both rotate at the same angle. FIGS. 9A-9B illustrate the case of the rotation of 90 degrees with respect to the pointed ends 320, where the rotated threading holes 50' extend along the circumferential direction of the tissue cutting stent 1. In this way, the first reefing thread 5 bends less after passing through all the first threading holes 50', thus when the first reefing thread 5 moves relative to the first threading holes 50', it encounters less resistance. It is convenient to avoid the tissue cutting stent cannot fully expand to a desired dimension due to the frictional resistance between the first reeling thread 5 and the first threading holes 50' when the tissue cutting stent expands from the contracted state to the expanded state. However, in other embodiments not shown, the pointed ends 320' may also rotate at any other angle. Those skilled in the art can make an appropriate rotation angle as needed, thereby adjusting the frictional coefficient of the sliding connection between the first threading holes 50' and the first reefing thread 5 as well as the closing effect of the tissue cutting stent 1. This threading manner of the first reefing thread 5 is referred to herein as annular threading manner.

In the preceding embodiment, in the case where the first reefing thread 5 is threaded at the distal end of the tissue cutting stent 1 to form the web-like structure, the lesioned tissues can be resected primarily using the first reefing thread 5 while it advances and aided by the edge of the distal end of the tissue cutting stent 1. In other embodiments, such as in the case of the Z-shaped threading manner and the annular threading manner, the resection of the lesioned tissues using the first reefing thread 5 and the edge of the distal end of the tissue cutting stent 1 is not particularly satisfactory. In this case, optionally, the tissue cutting stent 1 may be provided to be electrically conductive. At the same time, the first reefing thread 5 is also electrically conductive. In this way, the tissue cutting stent 1 and the first reefing thread 5 may form a positive electrode in an electrical circuit, which forms a monopolar electric knife circuit together with a negative plate affixed to the body surface, thereby electrical treatment such as electro-resection, electrocoagulation or radiofrequency ablation on the lesioned tissues can be performed while the tissue cutting stent 1 advances and during its expansion.

Figure 12:
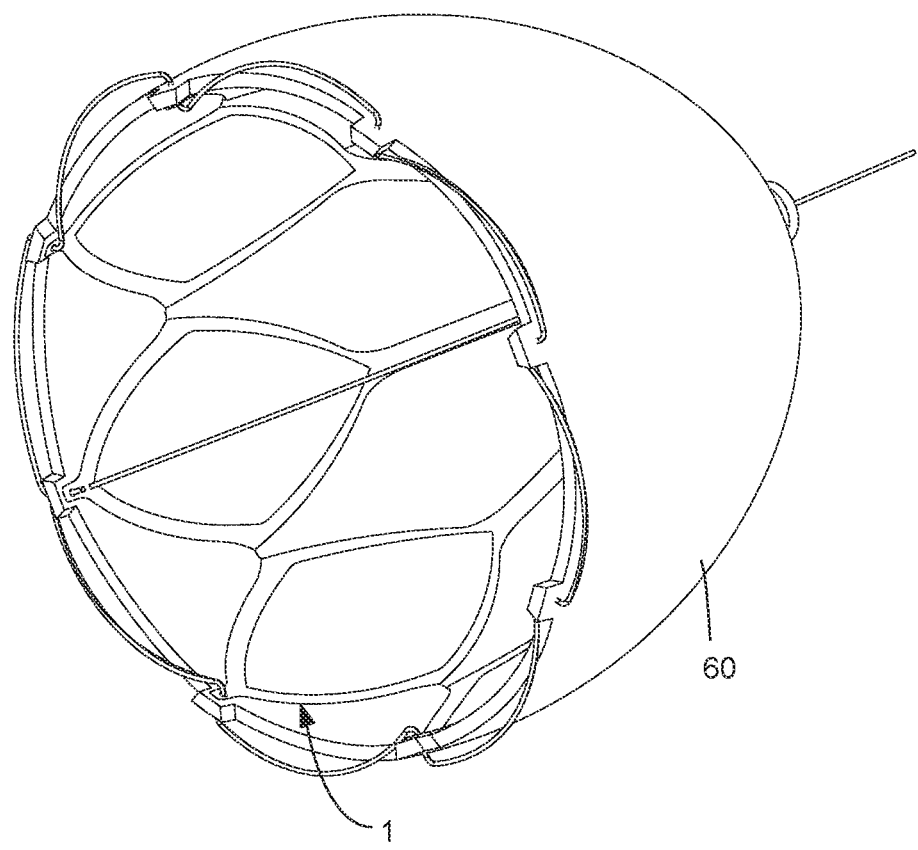
FIG. 12 is a schematic diagram of a tissue cutter according to the sixth exemplary embodiment of the present invention, wherein the tissue cutting stent is covered with a membrane.

In a further preferred embodiment, back to see FIGS. 1-3, the delivery sheath 3 is electrically conductive, which acts as one electrode, and the tissue cutting stent 1 and the first reefing thread 5 act as the other electrode, thereby forming a bipolar electric knife circuit. In this case, the outer surface of the tissue cutting stent 1 may be covered with an insulating outer layer 60, as shown in FIG. 12. And, the connector 4 and the pusher 6 are insulated from the delivery sheath 3. Optionally, the connector 4 and the pusher 6 may be made of an insulating material, or an insulating layer may be formed on the outer surfaces of the connector 4 and the pusher 6 as well. Thus, by forming the bipolar electric knife circuit, it is possible to electrify the tissue cutting stent 1 while advancing and expanding to electrically resect the lesioned tissues.

In another further preferred embodiment, the puncture needle 2 is electrically conductive, which acts as one electrode, and the tissue cutting stent 1 and the first reefing thread 5 act as the other electrode, thus forming the bipolar electric knife circuit. In this case, the delivery sheath 3 may be insulating. Optionally, the delivery sheath 3 may be made of an insulating material or an insulating layer may also be formed on the outer surface of the delivery sheath 3. Thus, by forming a bipolar electric knife circuit, it is possible to electrify the tissue cutting stent 1 while advancing and expanding to electrically resect the lesioned tissues.

By forming the monopolar electric knife circuit and the bipolar electric knife circuit as described above, electrocoagulation may be performed for hemostasis during or after tissue resection. In addition, the bipolar electric knife circuit has more stable electrical properties than the monopolar electric knife circuit. The ablation treatment may be performed at the external side of needle passage or resection area to kill locally scattered tumor cells that are not resected.

Figure 11A:
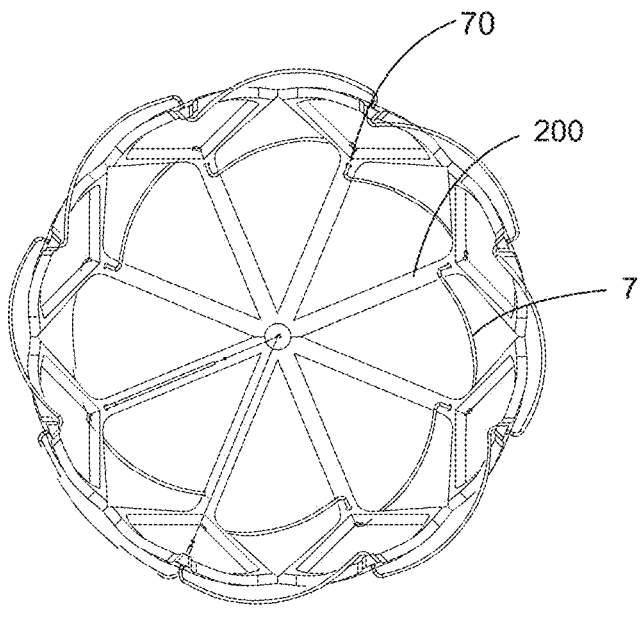
FIGS. 11A-11B are schematic diagrams of a tissue cutter from multiple angles according to the fifth exemplary embodiment of the present invention, respectively.
Figure 11B:
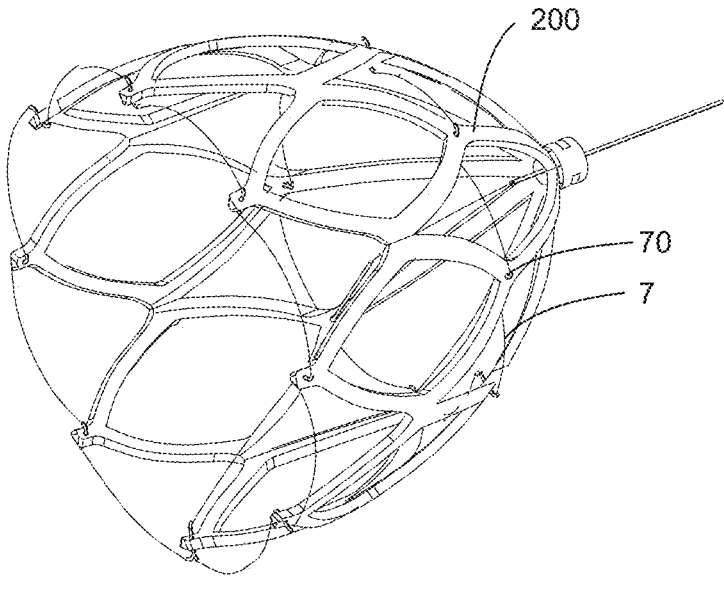

In another preferred embodiment, as shown in FIGS. 11A-11B, the support part 200 may be provided with a plurality of second threading holes 70, and the plurality of second threading holes 70 are arranged along the circumferential direction of the tissue cutting stent. Along the axial direction, the plurality of second threading holes 70 may be provided in the middle of the support part 200 or at the distal end of the support part 200. The tissue cutter further comprises a second reefing thread 7, and the second reefing thread 7 passes through the plurality of second threading holes 70. Thereby, the second reefing thread 7 may be pulled outside the body when the tissue cutting stent goes into or is in the closed state to further reduce the radial dimension of the closed tissue cutter and compress the resected tissues within the accommodating space, so that the closed tissue cutter can be taken out through a minor incision.

The second reefing thread 7 sequentially passes through the plurality of second threading holes 70 along the circumferential direction. The second reefing thread 7 may pass through each second threading hole 70 along the same direction. The second reeling thread 7 may also pass through each second threading hole 70 along a different direction, for example the second reefing thread 7 may pass through adjacent second threading holes 70 along the different directions. One end of the second reefing thread 7 is secured to one of the second threading holes 70, and the other end thereof passes through the accommodating space. In the case where the proximal end of the tissue cutting stent has a center hole, the other end thereof may pass out through the center hole, as shown in the drawings. In the case no center hole is provided, the other end may pass out at any appropriate location at the proximal end of the tissue cutting stent. In the embodiments not shown, the second reefing thread 7 may also pass through the second threading holes 70 in other threading manners. For example, the second reefing thread 7 may adopt any of the threading manners for the first reefing thread 5. The advantage of the second reeling thread 7 sequentially passing through the plurality of second threading holes 70 along the circumferential direction is that the second reefing thread 7 does not affect the utilization of the accommodating space.

Figure 13:
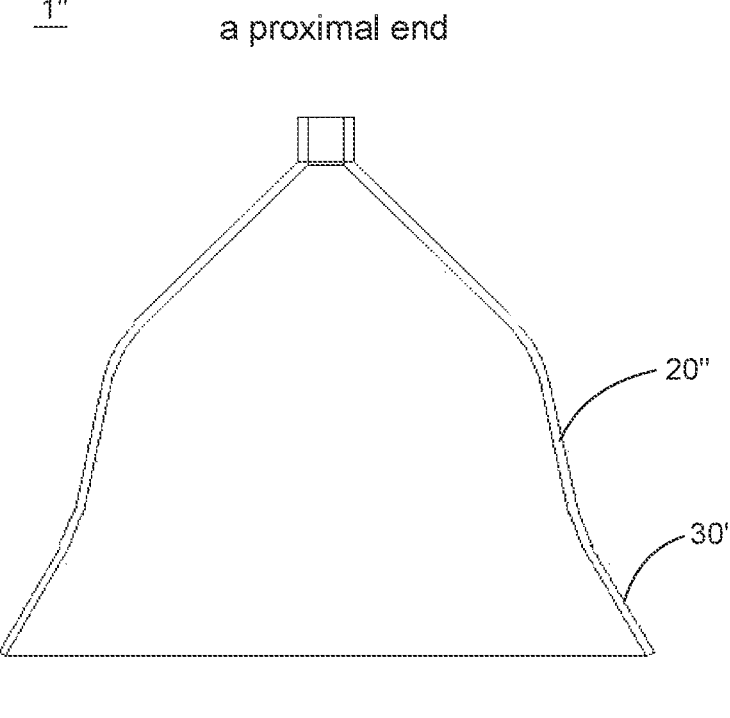
FIG. 13 is a schematic diagram of a tissue cutting stent according to another exemplary embodiment of the present invention.

FIG. 13 schematically illustrates a tissue cutting stent 1" according to another exemplary embodiment of the present invention, wherein the expansion part 30" of the tissue cutting stent 1" is gradually opens from its proximal end to its distal end. The expansion part 30" is at an angle to the overall direction of advancing (i.e. advancing along the direction of the axis P-P), thereby the expansion part 30" may expand in advance when the expansion part 30" has stretched out of the delivery sheath and the support part 20" not yet fully stretched out of the delivery sheath, to conduct preliminary resection of the tissues, thereby reducing the radial resistance to the tissue cutting stent in the process of its releasing and expansion and forming a more stable expansion dimension. Along the extension direction of the axis P-P, the intersection angles between various sections of the expansion part 30" and the axis P-P may be the same or different. In the case where the intersection angles are different, preferably, the angles between the expansion part 30" and the axis P-P may gradually increase along the direction from the proximal end to the distal end. It is more favorable for the expansion part 30" to expand and open within the tissues and organs.

Further preferably, the expansion part 30" bend outward with respect to the support part 20". The smaller angle between the support part 20" and the axis P-P can be ensured that the tissue cutting stent 1" has a sufficient axial dimension to form a sufficiently deep accommodating space. Where the angle between the expansion part 30" and the axis P-P is larger, the radial resistance to the expansion part 30" and the support part 20" in the process of expansion can be reduced to form a more stable expansion dimension.

Optionally, any of the aforesaid tissue cutting stents can further comprise a membrane. Referring to the embodiment as shown in FIGS. 4A-4C, for example. FIG. 12 illustrates the structure covered with the membrane, wherein the membrane may cover the support part 20 and the expansion prat 30. The membrane may comprise an inner layer, or an outer layer, or the both. The inner layer covers the inner surfaces of the support part 20 and the expansion part 30. The outer layer 60 (see FIG. 12) covers the outer surfaces of the support part 20 and the expansion part 30. With the support part 20 and the expansion part 30 covered with the membrane, the effective isolation of the lesioned tissues from the healthy tissues can be ensured during and after the resection process. From the perspective of isolating the lesioned tissues from the healthy tissues, it is not required that the membrane must be completely enclosed, as long as it can serve to isolate cells.

After the expansion part 30 is completely closed, the electric ablation treatment may continue to be exerted to inactivate the local tissues not resected. In this case, preferably, the outer layer may be an electrically conductive layer that participates in the ablation, and the inner layer may be an insulating layer that protects the biological properties of the resected tissues from being destroyed for use in pathological diagnosis.

Optionally, both the inner and outer layers may be insulating layers. In this way, the inner and outer layers may be the layers of the same material, resulting in simple processing technics and less cost.

Preferably, the fixed part 10 is provided with a through-hole 14, and the through-hole 14 is communicated with the center hole 12, as shown in FIG. 12. In the case where the support part 20 and the expansion part 30 are covered with the membranes, referring to FIGS. 1-3, airways may be formed within the delivery sheath 3 and on the outer side of the tissue cutting stent 1. During expansion, positive pressure gas may be delivered into the delivery sheath 3 from the proximal end and into the accommodating space via the through-hole 14 and the center hole 12. Since the front end of the tissue cutting stent 1 is located within the tissues and organs, the positive pressure gas can make the support part 20 and the expansion part 30 expand. After expansion and shaping, a negative pressure may be created within the delivery sheath 3 and the accommodating space, thereby drawing in more tissues to be resected.

Thus, in this case, the interventional surgical instrument further comprises a pneumatic device, and the pneumatic device is used to inject air to the delivery sheath 3 and/or extract air from the delivery sheath 3 to create the positive and negative pressures as described above.

In addition, in the case where the fixed part 10 is provided with the through-hole 14, when the tissue cutting stent 1 is in a push-out position, as shown in FIG. 2, the tissue cutting stent 1 does not separate from the delivery sheath 3 completely, but abuts against the edge of the distal opening of the delivery sheath 3. Since the fixed part 10 is continuously kept within the delivery sheath 3, no leakage of cellular tissues through the through-hole 14 is caused.

In another preferred embodiment, the distal end of the delivery sheath 3 may be provided with water-permeable holes (not shown), and the tissue cutting stent 1 may be covered with a water-resisting membrane. The space between the water-resisting membrane and the delivery sheath is communicated with the outside via the water-permeable holes. As a result, electrically conductive water may be delivered into the tissues and organs via the delivery sheath 3 and the water-permeable holes, thereby improving the electrical conductivity of the electrodes and making the electrical conductivity of the tissues and organs more uniform, which facilitates the execution of electro-resection. At the same time, the temperature of the local tissues can be reduced during the electro-resection. If the temperature of the surrounding tissues is too high in the process of the electro-resection, they may adhere to the tissue cutting stent 1. With the delivery of fluid, not only the temperature of the tissues and the tissue cutting stent 1 can be lowered, but also the tissues can be moisturized so as to prevent the tissue cutting stent 1 from being adhered to the tissues.

Figure 14A:
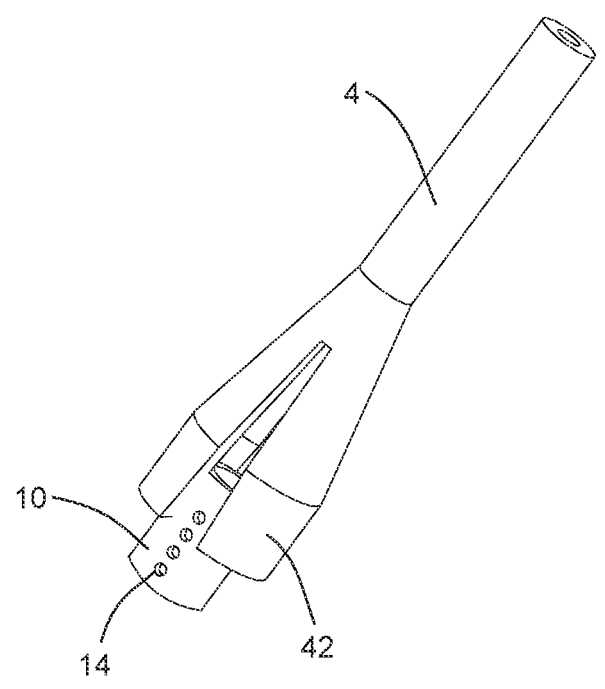
FIGS. 14A-14B are schematic diagrams of a connector assembled with a fixed part according to one exemplary embodiment of the present invention, respectively.
Figure 14B:
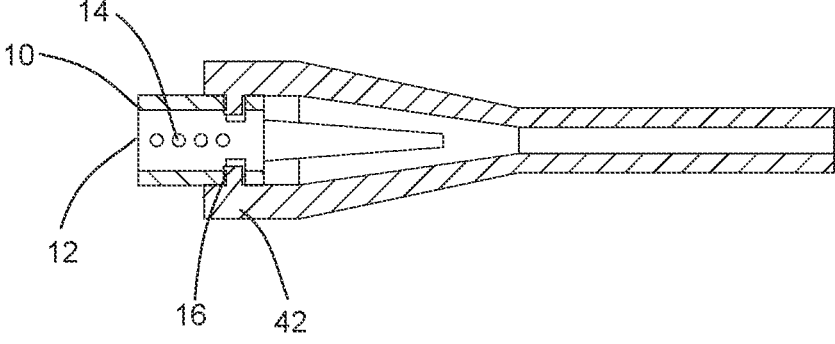

FIGS. 14A-14B also illustrate a connector 4 according to an embodiment of the invention. The connector 4 may be provided with a plurality of snap clips 42 at the distal end, and the plurality of snap clips 42 arranged along the circumferential direction. A gap is formed between adjacent snap clips 42, thereby allowing the snap clips 42 to have a certain degree of elasticity. The fixed part 10 may be provided with openings 16 corresponding to the snap clips 42. When a radially outward force is exerted on the snap clips 42, the snap clips 42 may open and snap into the openings 16.

Figure 15A:
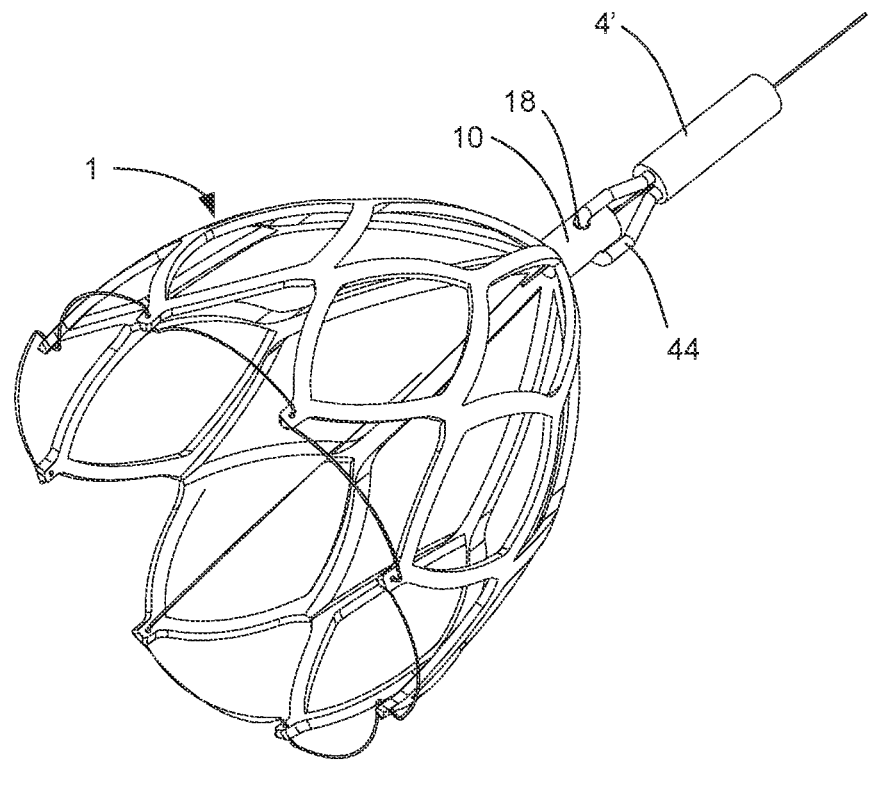
FIGS. 15A-15B are schematic diagrams of a connector assembled with a tissue cutter according to one exemplary embodiment of the present invention, respectively.
Figure 15B:
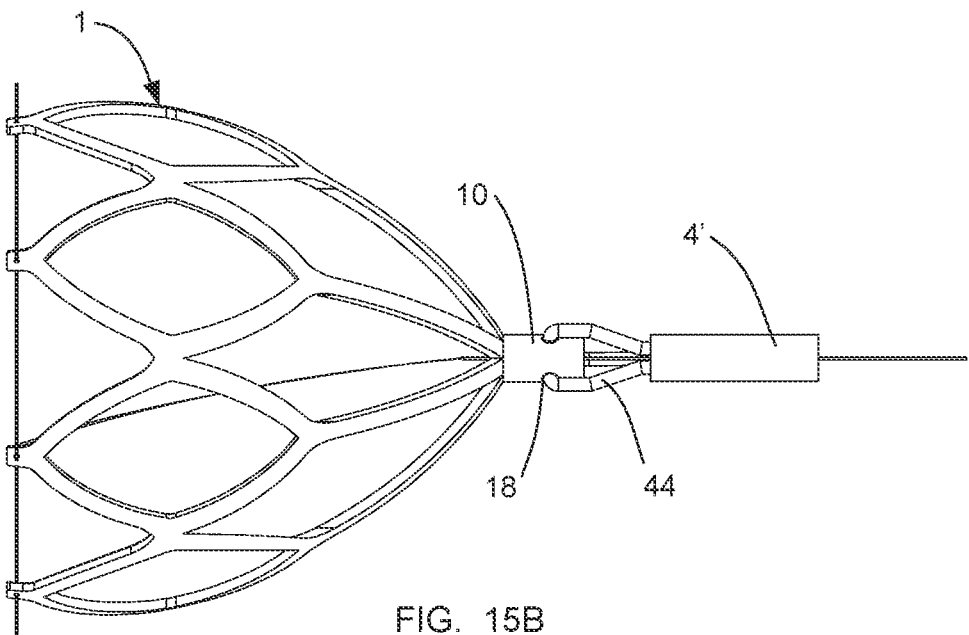

FIGS. 15A-15B illustrate a connector 4' according to another embodiment of the invention. The connector 4' comprises a plurality of elastic locking claws 44, and the outer side of the fixed part 10 of the tissue cutting stent 1 is provided with a plurality of slots 18. When the connector 4' is within the delivery sheath 3, as shown in FIGS. 1-3, the plurality of elastic locking claws 44 are compressed along the radial direction, that is, the elastic locking claws 44 are subjected to a radially inward force exerted by the delivery sheath 3. Here, the plurality of elastic locking claws 44 snap with the plurality of slots 18, respectively. When the plurality of elastic locking claws are outside the delivery sheath 3, the plurality of elastic locking claws 44 are separated from the plurality of slots 18 along the radial direction. As a result, after the pusher 6 pushes the connector 4 out of the delivery sheath 3, the radial force exerted by the delivery sheath 3 is removed, thereby making the connector 4 separated from the tissue cutting stent 1.

Optionally, at least one of the puncture needle 2, the delivery sheath 3 and the first reefing thread 5 is provided with scales. The puncture needle 2 and the delivery sheath 3 may have scales on their outer surfaces which can help the surgeon to determine how deep they have entered the tissues and organs. The first reefing thread 5 may have scales on the section remaining outside the body, which can prompt the surgeon the current degree of closing of the tissue cutting stent 1.

The minimally invasive interventional surgical instrument may be used in following ways.

Under the guidance of imaging devices (such as CT), the minimally invasive interventional surgical instrument reaches the target tissues via a puncture route. It may be also reach the vicinity of the target tissues via a natural cavity, and later approach the lesions with local puncturing.

After puncturing, the delivery sheath 3 may be delivered inside the patients' body by the puncture needle 2, or re-enters via the incision after the puncture needle 2 is withdrawn, thereby making it possible to use the puncture needle 2 with a smaller diameter.

The tissue cutting stent 1 or 1' is pushed out of the delivery sheath 3 by the pusher 6 and then may spread with self-expanding, or under the positive pressure, it may reach an expended state in the tissues and organs, as shown in FIG. 2. In the expansion process, the tissue cutting stent 1 or 1' may be energized to reduce the expansion resistance. Since the distal end of the tissue cutting stent 1 or 1' separates from the delivery sheath 3, the distal end of the tissue cutting stent

1 or 1' spreads firstly, and electrification allows the distal end to have a resecting effect, i.e., resecting while spreading.

After the tissue cutting stent 1 or 1' expands, it may continue to be pushed straight forward, and with mechanical resecting and/or electrical resecting, to enclose the lesioned tissues into the accommodating space of the tissue cutting stent 1 or 1'. It may rotate and draw the lesioned tissues during the process of resecting to increase the mechanical resecting intensity. In the process of resecting, the accommodating space may continue to be kept under the negative pressure by the aforesaid pneumatic device to draw and fix more tissues into the accommodating space. In the process of resecting tissues, electro-resection mode or electrocoagulation mode may be used alone, or a combination of electro-resection and electrocoagulation modes may be used to meet different needs for resection and hemostasis.

The first reefing thread 5 is lifted after the lesioned tissues are enclosed in the accommodating space, and whether the tissue cutting stent 1 or 1' has been fully closed may be determined based on the length of the lifting. In the process of lifting, different electrosurgical modes such as electro-resection, electrocoagulation or vascular closure may continue to be exerted. After the tissue cutting stent 1 or 1' is completely closed, electric ablation may continue to be exerted to inactivate the local tissues not resected.

If the tissues are compressible, the tissue cutting stent 1 or 1' may be retracted into the delivery sheath 3 by lifting the pusher 6 after the tissue cutting stent 1 or 1' is completely closed, which allows the tissue cutting stent 1 or 1' to be completely wrapped and then removed from the body, reducing the risk of lesion metastasis. Alternatively, the tissue cutting stent 1 or 1' may be directly lifted after being secured to the delivery sheath 3 and the pusher 6 to take all the tissues out. Optionally, the puncture needle 2 may be left in the body for subsequent processing, such as injection of hemostatic drugs and so on.

If the tissue cutting stent 1 or 1' is retained in the patient's body, the pusher 6 may be continuously pushed until the connector 4' is pushed out of the delivery sheath 3 to be unlocked. After the puncture needle 2, the delivery sheath 3, the connector 4' and the pusher 6 are retracted, the tissue cutting stent 1 or 1' and the first reefing thread 5 are retained in the body which may be taken out by other surgeries. If the tissue cutting stent 1 or 1' is self-degrading, after the first reefing thread 5 is unlocked from the tissue cutting stent 1 or 1', the first reefing thread 5 can be withdrawn from the body, or the portion of the first reefing thread 5 left outside the stent can be cut off by using a cutting device.

The present invention has been illustrated by the above embodiments, but it should be understood that the above embodiments are used only for the purpose of giving examples and illustration, but not intended to limit the invention to the scope of the described embodiments. Furthermore, it can be understood by those skilled in the art that the present invention is not limited to the above-described embodiments, and that a greater variety of variations and modifications may be made in accordance with the teachings of the present invention, all of which fall into the scope of protection claimed by the present invention. The scope of protection of the present invention is defined by the appended claims as well as their equivalent scope.

What is claimed is:

1. A tissue cutter, characterized in that it comprises:
    a tissue cutting stent, the tissue cutting stent being expandable in a radial direction, the expanded tissue cutting stent being shaped so as to gradually open from a proximal end to a distal end such that the outer diameter of the distal end is larger than the outer diameter of the proximal end, and an accommodating space being formed inside the expanded tissue cutting stent and having a shape corresponding to the shape of the expanded tissue cutting stent, the tissue cutting stent provided with a plurality of first threading holes at the distal end, the plurality of first threading holes arranged along a circumferential direction of the tissue cutting stent; and a first reefing thread, the first reefing thread passing through the plurality of first threading holes, the first reefing thread having opposite first and second ends, the first end secured to a starting threading hole in the plurality of first threading holes, wherein:

the first reefing thread and the distal end of the tissue cutting stent are used for resecting tissues;

the tissue cutting stent comprises a fixed part, a support part and an expansion part, the fixed part, the support part and the expansion part connected sequentially along the axial direction of the tissue cutting stent, from the proximal end to the distal end, the support part and the expansion part are expandable along the radial direction to form the accommodating space, wherein the expanded support part diverges in a branched or radial manner; and the expansion part is closed when the first reefing thread is pulled, such that the resected tissues are wrapped in the accommodating space.

2. The tissue cutter according to claim 1, characterized in that the plurality of first threading holes are provided on the expansion part.

3. The tissue cutter according to claim 2, characterized in that the expansion part and the support part are in a web-like structure overall.

4. The tissue cutter according to claim 2, characterized in that the support part comprises a plurality of support segments provided along the circumferential direction of the tissue cutting stent, each of the plurality of support segments having a root end and a tip end, the root end connected to the fixed part and the tip end connected to the expansion part.

5. The tissue cutter according to claim 4, characterized in that the expansion part has a single layer or multiple layers of annular structure, each layer of annular structure comprising a plurality of expansion segments provided along the circumferential direction of the tissue cutting stent, each expansion segment being V-shaped to make each expansion segment having two open ends and one pointed end, the open ends of adjacent two expansion segments in each layer of annular structure being connected, wherein in the case where the expansion part has a single layer of annular structure, the open ends are connected to the tip ends of the plurality of support segments in one-to-one correspondence, the pointed end of each expansion segment is provided with one of the first threading holes;

in the case where the expansion part has multiple layers of annular structure, the multiple layers of annular structure are provided along the axial direction, wherein in adjacent two layers of annular structure, the open ends of one layer of annular structure and the pointed ends of the other layer of annular structure are connected in one-to-one correspondence; and wherein, the open ends of the layer of annular structure closest to the support segments are connected to the tip ends of the plurality of support segments in one-to-one correspondence, and the pointed ends of each expansion segment of the layer of annular structure farthest from the support segments are all provided with one of the first threading holes.

6. The tissue cutter according to claim 4, characterized in that each of the plurality of the support segments is rod-shaped, wherein in an expanded support part, the plurality of the support segments are radial from the root ends to the tip ends.

7. The tissue cutter according to claim 4, characterized in that in the expanded support part, each of the plurality of support segments is Y-shaped to make each of the plurality of support segments comprise one root end and two tip ends, wherein the root ends of the plurality of support segments are clustered with each other, and in any adjacent two support segments, one tip end of one support segment is connected to one tip end of the other support segment.

8. The tissue cutter according to claim 4, characterized in that the pointed ends provided with the first threading holes rotate a predetermined angle in a plane perpendicular to the axial direction to make the first threading holes be at the predetermined angle to the radial direction of the tissue cutting stent.

9. The tissue cutter according to claim 2, characterized in that the support part is provided with a plurality of second threading holes, the plurality of second threading holes arranged along the circumferential direction of the tissue cutting stent, and the tissue cutter further comprises a second reefing thread, the second reefing thread passing through the plurality of second threading holes.

10. The tissue cutter according to claim 9, characterized in that the second reefing thread sequentially passes through the plurality of second threading holes along the circumferential direction, one end of the second reefing thread is secured to one of the plurality of second threading holes.

11. The tissue cutter according to claim 2, characterized in that the fixed part, the support part and the expansion part are formed by cutting a tubular product in the axial direction.

12. The tissue cutter according to claim 2, characterized in that the support part and the expansion part have a self-expending function.

13. The tissue cutter according to claim 1, characterized in that the expansion part bends radially outward with respect to the support part.

14. The tissue cutter according to claim 1, characterized in that the proximal end of the tissue cutting stent has a center hole, which is communicated to the accommodating space along the axial direction, and a second end of the first reefing thread passes out from inside the accommodating space via the center hole.

15. The tissue cutter according to claim 14, characterized in that the proximal end of the tissue cutting stent is further provided with a through-hole, and the through-hole is communicated with the center hole.

16. The tissue cutter according to claim 1, characterized in that a middle section of the first reefing thread sequentially passes through other threading holes in the plurality of first threading holes along the circumferential direction.

17. The tissue cutter according to claim 16, characterized in that the middle section of the first reefing thread passes through other threading holes in the plurality of first threading holes along the same direction.

18. The tissue cutter according to claim 1, characterized in that a middle section of the first reefing thread passes through other threading holes in the plurality of first threading holes in a crisscross manner to make the first reefing thread form the web-like structure at the distal end of the tissue cutting stent.

19. The tissue cutter according to claim 1, characterized in that the tissue cutting stent further comprises a membrane, which covers the support part and the expansion part.

20. The tissue cutter according to claim 19, characterized in that the membrane comprises an inner layer and/or an outer layer, the inner layer covering the inner surfaces of the support part and the expansion part, the outer layer covering the outer surfaces of the support part and the expansion part, the inner layer being an insulating layer, the outer layer being an electrically conductive or insulating layer.

21. A minimally invasive interventional surgical instrument, characterized in that the minimally invasive interventional surgical instrument comprises:

the tissue cutter according to claim 1;

a delivery sheath, the contracted tissue cutting stent accommodated within the delivery sheath, the delivery sheath having a proximal opening at its proximal end and a distal opening at its distal end;

a pusher; and a connector, connected between the pusher and the distal end of the tissue cutting stent;

wherein, the pusher extends into the delivery sheath from the proximal opening of the delivery sheath to push the tissue cutting stent out from the distal opening of the delivery sheath.

22. The minimally invasive interventional surgical instrument according to claim 21, characterized in that the connector comprises a plurality of elastic locking claws, an outer side of the proximal end of the tissue cutting stent is provided with a plurality of slots, wherein where the connector is located within the delivery sheath, the plurality of elastic locking claws are compressed along the radial direction, and the compressed plurality of elastic locking claws snap with the plurality of the slots, respectively, where the plurality of the elastic locking claws are located outside the delivery sheath, the plurality of elastic locking claws are separated from the plurality of the slots along the radial direction.

23. The minimally invasive interventional surgical instrument according to claim 21, characterized in that the first reefing thread and the tissue cutting stent are electrically conductive.

24. The minimally invasive interventional surgical instrument according to claim 23, characterized in that the delivery sheath is electrically conductive, the outer surface of the tissue cutting stent is covered with an insulating outer layer, and the connector and the pusher are insulated from the delivery sheath.

25. The minimally invasive interventional instrument according to claim 21, characterized in that the distal end of the delivery sheath is provided with water-permeable holes, the tissue cutting stent is covered with a water-resisting membrane, and a space between the water-resisting membrane and the delivery sheath is communicated with the outside via the water-permeable holes.

26. The minimally invasive interventional instrument according to claim 21, characterized in that the minimally invasive interventional instrument further comprises a puncture needle, and the delivery sheath is accommodated within the puncture needle.

27. The minimally invasive interventional instrument according to claim 26, characterized in that the first reefing thread and the tissue cutting stent are electrically conductive, the puncture needle is electrically conductive, and the delivery sheath is insulating.

28. The minimally invasive interventional instrument according to claim 26, characterized in that at least one of the puncture needle, the delivery sheath and the first reefing thread is provided with scales.

29. The minimally invasive interventional instrument according to claim 21, characterized in that in the case where the proximal end of the tissue cutting stent has a center hole, the fixed part is provided with a through-hole and the through-hole is communicated with the center hole, the minimally invasive interventional instrument further comprises a pneumatic device, and the pneumatic device is used to inject air to the delivery sheath and/or extract air from the delivery sheath.

* * * * *